(12) United States Patent
Mannarino et al.

(10) Patent No.: US 12,109,759 B2
(45) Date of Patent: Oct. 8, 2024

(54) SYSTEM FOR PRODUCING A GRAFT DEVICE WITH A THREE DIMENSIONAL COVERING

(71) Applicant: Xeltis AG, Zurich (CH)

(72) Inventors: Matthew Mannarino, Taunton, MA (US); Jon McGrath, Duxbury, MA (US); Cory Leeson, Taunton, MA (US); Mohammed El-Kurdi, Mansfield, MA (US); Danielle McDowell, Taunton, MA (US); Kermit Santiago, Taunton, MA (US); J. Christopher Flaherty, Taunton, MA (US)

(73) Assignee: Xeltis AG, Zurich (CH)

( * ) Notice: Subject to any disclaimer, the term of this patent is extended or adjusted under 35 U.S.C. 154(b) by 42 days.

(21) Appl. No.: 18/120,260

(22) Filed: Mar. 10, 2023

(65) Prior Publication Data

US 2023/0356468 A1    Nov. 9, 2023

Related U.S. Application Data

(62) Division of application No. 16/308,216, filed as application No. PCT/US2017/036800 on Jun. 9, 2017, now abandoned.
(Continued)

(51) Int. Cl.
*B29C 64/386*    (2017.01)
*A61F 2/06*    (2013.01)
(Continued)

(52) U.S. Cl.
CPC .............. *B29C 64/386* (2017.08); *A61F 2/06* (2013.01); *A61M 1/3655* (2013.01);
(Continued)

(58) Field of Classification Search
CPC ......... B29C 64/386; B29C 64/10; A61F 2/06; A61F 2240/002; A61M 1/3655;
(Continued)

(56) References Cited

U.S. PATENT DOCUMENTS 9,469,075 B2 * 10/2016 Zachariasen ........... B33Y 30/00
2009/0297582 A1 * 12/2009 Meyer ................ A61B 17/1215
156/60

(Continued)

FOREIGN PATENT DOCUMENTS

WO   WO-2015073925 A2 *  5/2015   ............... A61F 2/07
WO   WO-2015100238 A1 *  7/2015   ............... A61F 2/06

*Primary Examiner* — Susan S Su
*Assistant Examiner* — Eric Rassavong

(57) ABSTRACT

A system for producing a graft device for a patient may comprise: an imaging device configured to produce image data of a tubular conduit; and a processing unit configured to receive the image data from the imaging device. The processing unit may comprise an algorithm configured to process the image data, and produce a construction signal based on the image data. A material delivery device may be configured to receive the construction signal from the processor, and deliver material to produce a 3D covering based on the construction signal. The graft device may comprise the 3D covering positioned about the tubular conduit. Graft devices and methods of producing graft devices may also be provided.

3 Claims, 4 Drawing Sheets

Related U.S. Application Data

(60) Provisional application No. 62/348,318, filed on Jun. 10, 2016.

(51) Int. Cl.
*A61M 1/36* (2006.01)
*A61M 27/00* (2006.01)
*B29C 64/10* (2017.01)
*B33Y 10/00* (2015.01)
*B33Y 30/00* (2015.01)
*B33Y 50/00* (2015.01)
*B33Y 80/00* (2015.01)
*B29L 31/00* (2006.01)

(52) U.S. Cl.
CPC ........... *A61M 27/002* (2013.01); *B29C 64/10* (2017.08); *B33Y 10/00* (2014.12); *B33Y 30/00* (2014.12); *B33Y 50/00* (2014.12); *B33Y 80/00* (2014.12); *A61F 2240/002* (2013.01); *A61M 2207/00* (2013.01); *A61M 2207/10* (2013.01); *B29L 2031/7534* (2013.01)

(58) Field of Classification Search
CPC ........... A61M 27/002; A61M 2207/00; A61M 2207/10; B33Y 10/00; B33Y 30/00; B33Y 50/00; B33Y 80/00; B29L 2031/7534

See application file for complete search history.

(56) References Cited

U.S. PATENT DOCUMENTS

| | | | |
|---|---|---|---|
| 2014/0088618 A1* | 3/2014 | Song | A61F 2/0063 606/151 |
| 2015/0209162 A1* | 7/2015 | Verschueren | B29C 64/386 264/250 |
| 2015/0314532 A1* | 11/2015 | Gordon | B33Y 30/00 425/174 |
| 2016/0129637 A1* | 5/2016 | Zhou | G05B 15/02 700/98 |
| 2016/0148372 A1* | 5/2016 | Itu | A61B 6/507 382/128 |
| 2016/0325480 A1* | 11/2016 | Soletti | A61F 2/06 |
| 2016/0371835 A1* | 12/2016 | Grbic | A61B 34/10 |
| 2018/0368968 A1* | 12/2018 | Leeson | D01D 5/0038 |

* cited by examiner

SYSTEM FOR PRODUCING A GRAFT DEVICE WITH A THREE DIMENSIONAL COVERING

CROSS-REFERENCE TO RELATED APPLICATIONS

This application is a divisional of U.S. patent application Ser. No. 16/308,216 filed Dec. 7, 2018, which is incorporated herein by reference. U.S. patent application Ser. No. 16/308,216 is a 371 of PCT/US2017/036800 filed Jun. 9, 2017. PCT/US2017/036800 claims the benefit of U.S. Provisional Application Ser. No. 62/348,318 filed Jun. 10, 2016, the contents of which are incorporated herein in their entirety.

FIELD OF THE INVENTION

The invention relates to methods and systems for producing graft devices.

BACKGROUND OF THE INVENTION

Devices in the field of rapid prototyping, using 3D computer aided design (CAD) data, can be used to produce various three-dimensional (3D) structures. These devices use geometric data, either as 3D solid models, or 2D slices using a scanning device, to produce a scale model, a physical part, or an assembly via either an additive or subtractive manufacturing method.

In the field of tissue engineering, 3D printers are used to produce scaffolds, which can be subsequently seeded with cells, cultured ex vivo, and then implanted as tissue replacements. Another approach is 3D bioprinting, which can be used to fabricate living tissue constructs by incorporating living cells into a scaffold created during the fabrication process.

Current 3D printed implants are not customized to conform to patient specific anatomical geometries, resulting in various limitations. There is a need for improved graft devices, and other three-dimensional implantable structures, that provide long term efficacy and safety.

SUMMARY OF THE INVENTION

For these and other reasons, there is a general need for systems, devices and methods that can provide enhanced implantable devices for mammalian patients. Desirably, the systems, devices and methods may improve long term efficacy and minimize surgical and device complications such as those caused by improper or inadequate production of an implantable device.

Embodiments of the systems, devices and methods described herein can be directed to systems, devices and methods for producing graft devices and other devices for implanting in mammalian patients, as well as to the implantable devices themselves.

According to an aspect of the present disclosure, a system for producing a graft device for a patient may comprise an imaging device configured to produce image data of a tubular conduit, and a processing unit configured to receive the image data from the imaging device. The processing unit can comprise an algorithm, the algorithm configured to process the image data, and produce a construction signal based on the image data. The system may comprise a material delivery device configured to receive the construction signal from the processor, and deliver material to produce a 3D covering based on the construction signal. The graft device may comprise the 3D covering positioned about the tubular conduit.

In some cases, the material delivery device may be configured to deliver the 3D covering onto the tubular conduit. In some cases, the 3D covering may be configured to be positioned about the tubular conduit after being produced by the material delivery device. In some cases, the graft device may comprise a coronary artery bypass graft. In some cases, the graft device may comprise a dialysis graft.

In some cases, the graft device may comprise an implant selected from the group consisting of: artery bypass graft; coronary artery bypass graft; dialysis graft; peripheral arterial bypass graft; great vessel replacement; great vessel bypass graft; esophageal graft; tracheal graft; bronchial graft; biliary duct graft; intestinal graft; organ transplant vascular connection graft; neuronal replacement implant; ligament graft; ligament replacement; tendon graft; tendon replacement; transplant organ coating; fallopian tube; urethra; ureter; cartilage; hip joint; shoulder joint; intervertebral disc; menisci; and any combination thereof.

In some cases, the imaging device may comprise a device selected from the group consisting of: computerized tomography (CT) imager; optical coherence tomography (OCT) imager; magnetic resonance imaging (MM); 3D Scanner; Camera; Infrared Camera; Ultrasound imager; and any combination thereof.

In some cases, the image data may comprise information related to the tubular conduit. In some cases, the image data may comprise information related to a portion of the patient's anatomy. In some cases, the image data may comprise data collected when the tubular conduit is in-situ. The image data can comprise data collected after the tubular conduit is harvested from the patient. In some cases, the image data may comprise data collected after the tubular conduit is harvested from the patient. In some cases, the image data may comprise data selected from the group consisting of: surface topography data; surface geometry data; periphery data; length data; diameter data; thickness data such as wall thickness data; taper data; eccentricity data; relative position data; trajectory data; speed of motion data; relative angle data; radiopacity data; blood flow data; echographic data; spectroscopic data; and any combination thereof.

In some cases, the image data may comprise at least one discrete feature of the tubular conduit. The at least one discrete feature can be identified by the algorithm. The at least one discrete feature can comprise a feature selected from the group consisting of: sidebranch; recess; projection; end; end portion; bend portion; lobe; bifurcation; trifurcation; a dilated portion; a swollen portion; valve; a tapered portion; a location of a surgical staple; an angled portion; a calcified tissue portion; an atheromatous tissue portion; a partially occluded portion; a fully occluded portion; and any combination thereof. The at least one discrete feature can comprise a sidebranch. The image data can include sidebranch information selected from the group consisting of: location; diameter; taper angle; ligation device position; ligation device geometry; ligation device type; and any combination thereof.

In some cases, the image data may comprise information related to the compliance of the tubular conduit. In some cases, the image data may comprise information related to the shape of the tubular conduit changing over time. The information related to the shape of the tubular conduit changing over time can comprise information related to the shape of the tubular conduit changing over time prior to harvesting. The tubular conduit can change shape due to a change in to a parameter selected from the group consisting of: blood pressure; respiration; patient movement; and any combination thereof.

In some cases, the tubular conduit may comprise tissue selected from the group consisting of: cylindrical tissue; organ tissue; saphenous vein; vein; artery; urethra; intestine; esophagus; ureter; trachea; bronchi; duct; fallopian tube; and any combination thereof. In some cases, the tubular conduit may comprise tissue selected from the group consisting of: bone; ligament; tendon; and any combination thereof. In some cases, the tubular conduit may comprise artificial material.

In some cases, the processing unit may comprise memory circuitry. The memory circuitry can be configured to store information selected from the group consisting of: tissue type; type of the material; information regarding the application of the graft device; information regarding use of one or more tools; compliance information; density information; strength information; modulus of elasticity information; elastic limit information; wall thickness information; shrinkage information of the material; cure time information of the material; spacing to a mandrel and/or other target; minimum bend radius of the covering; maximum ovality of the covering; and any combination thereof. The construction signal can be based on information stored in the memory circuitry. In some cases, the processing unit may comprise at least one of a microprocessor or a microcontroller.

In some cases, the algorithm may be configured to identify at least one discrete feature of the tubular conduit. The at least one discrete feature of the tubular conduit identified by the algorithm can comprise a feature selected from the group consisting of: sidebranch; recess; projection; end; end portion; bend portion; lobe; bifurcation; trifurcation; a dilated portion; a swollen portion; valve; a tapered portion; a location of a surgical staple; an angled portion; a calcified tissue portion; an atheromatous tissue portion; a partially occluded portion; a fully occluded portion; and any combination thereof. The 3D covering can comprise at least one customized portion positioned relative to the at least one discrete feature. The customized portion can be positioned proximate the at least one discrete feature. The algorithm can be configured to identify at least two discrete features of the tubular conduit, and the 3D covering can comprise at least two customized portions. The customized portion can comprise a differentiating property selected from the group consisting of: different thickness; different material; different porosity; different pore size; different compliance in one or more directions; different level of conformality; different texture; different alignment and/or orientation of the deposited material; different stiffness; different fiber diameter; addition of a kink-resisting element; addition of an agent; and any combination thereof. The at least one discrete feature can comprise a protrusion of the tubular conduit. The protrusion can comprise a sidebranch. The 3D covering can comprise a customized portion including a void proximate the protrusion. The void can comprise a hole. The void can comprise a recess. The at least one customized portion can comprise a portion selected from the group consisting of: a portion comprising a change in deposition of the material such as to mechanically reinforce and/or provide a strain relief at a sidebranch location; a portion configured to constrain a sidebranch such as to minimize hemodynamic disruption in a lumen of the tubular conduit; and any combination thereof. The 3D covering can comprise a customized portion including a fillet positioned proximate the at least one discrete feature. The at least one discrete feature can comprise an end of the tubular conduit. The 3D covering can comprise a customized portion including a taper located proximate the end of the tubular conduit. The at least one discrete feature can comprise a second end of the tubular conduit, and the 3D covering can comprise a second customized portion including a second tapered positioned proximate the second end of the tubular conduit. The 3D covering can comprise a customized portion including a reinforced portion located proximate the end of the tubular conduit. The 3D covering can comprise a customized portion including an optimized anastomosis portion located proximate the end of the tubular conduit. The optimized anastomosis portion can comprise an optimized shape. The optimized anastomosis portion can comprise an optimized structure. The at least one discrete feature can comprise tissue whose softness is above a threshold. The customized portion can comprise a differentiating property selected from the group consisting of: different material; different compliance; different thickness; different permeability; different porosity; different anisotropy; and any combination thereof. The at least one discrete feature can comprise tissue whose flexibility is above a threshold. The customized portion can comprise a differentiating property selected from the group consisting of: different material; different compliance; different thickness; different permeability; different porosity; different anisotropy; and any combination thereof. The at least one discrete feature can comprise tissue whose shape changes over time. The customized portion can comprise a differentiating property selected from the group consisting of: different material; different compliance; different thickness; different permeability; different porosity; different anisotropy; and any combination thereof. The 3D covering can include a customized portion including a reinforced portion. The at least one discrete feature can comprise a thin-walled portion of the tubular conduit, and the customized portion can be located proximate the thin-walled portion. The 3D covering can include a customized portion including a strain relief. The at least one discrete feature can comprise at least one of an end of the tubular conduit or a bend portion of the graft device, and the customized portion can be located proximate the at least one discrete feature. The 3D covering can include a customized portion including modified porosity. The at least one discrete feature can comprise an anastomosis site and/or a segment of high curvature of the graft device, and the customized portion can be located proximate the at least one discrete feature. The 3D covering can include a customized portion including a modified compliance. The modified compliance can comprise a modified radial compliance. The modified compliance can comprise a modified axial compliance. The at least one discrete feature can comprise an anastomosis site, a ligament attachment site, a tendon attachment site and/or a site of segmented compliance, and the customized portion can be located proximate the at least one discrete feature.

In some cases, the algorithm may be configured to create a 3D model of the tubular conduit based on the image data. The 3D model can comprise a spatial model. The algorithm can be configured to modify the 3D model of the tubular conduit. The image data can comprise multiple slices of a CT image. In some cases, the algorithm may be configured to create a 3D model of a proposed 3D cover.

In some cases, the algorithm may be configured to create a proposed 3D model of the 3D covering, and to modify the proposed 3D model to create a final 3D model of the 3D covering. The algorithm can be configured to modify the proposed 3D model based on at least one discrete feature of the tubular conduit. The algorithm can be configured to modify the proposed 3D model based on user input.

In some cases, the algorithm may be configured to create a 3D model of at least one of the tubular conduit or the 3D covering based on boundary conditions. The algorithm can be configured to optimize hemodynamics within the tubular conduit by performing a function selected from the group consisting of: reducing flow turbulence; controlling bending radius; controlling lumen geometry; controlling a transition; controlling a taper; controlling a bend portion; controlling tortuosity; controlling wall shear; preventing buckling; optimizing wall shear stress; modifying an end portion to optimize an anastomotic connection; reducing geometric mismatch near an anastomotic connection; and any combination thereof.

In some cases, the algorithm may be configured to convert information from an imaging coordinate system to a material deposition coordinate system. The imaging coordinate system can comprise Cartesian coordinates and the material deposition coordinate system can comprise a cylindrical, spherical and/or curvilinear coordinate system.

In some cases, the material delivery device may comprise at least one nozzle, and the algorithm may be configured to create a pathway of motion for the at least one nozzle. The algorithm can create the pathway of motion based on one or more off limits locations. The pathway of motion can avoid portions of the 3D covering that have already been created. The pathway of motion can avoid the tubular conduit. The material delivery device can comprise a mandrel, and the pathway of motion can avoid the mandrel. The pathway of motion can minimize dissipation of heat to the tubular conduit. The pathway of motion can reduce multiple passes of delivery of material in neighboring regions of the tubular conduit within a time period.

In some cases, the algorithm may be configured to perform a self-diagnostic. The system can comprise at least one sensor configured to produce a signal, and the self-diagnostic can be based on the signal from the at least one sensor. The sensor can comprise one or more sensors selected from the group consisting of: an optical sensor; a laser; a magnetic sensor; an electrical sensor; an energy sensor; a pressure sensor; a force sensor; a strain gauge; a position sensor; a flow sensor; a sound sensor; an ultrasound sensor; a humidity sensor; and any combination thereof. The self-diagnostic can be configured to assess a parameter selected from the group consisting of: electrical connection status; rotational speed; translational speed; nozzle status; material delivery status; temperature; chamber environment condition; energy delivered; home position; a distance between two components of the system; and any combination thereof.

In some cases, the algorithm may be configured to create the construction signal based on a property of the tubular conduit. The construction signal can produce a 3D covering that provides mechanical support to the tubular conduit. The construction signal can produce a 3D covering with varied properties along a length of the tubular conduit.

In some cases, the material delivery device may comprise at least one nozzle. The material delivery device can comprise at least two nozzles. In some cases, the material delivery device may comprise a 3D printer. In some cases, the material delivery device may be configured to deliver the material using an additive printing process. In some cases, the material delivery device may be configured to deliver the material as a series of layers.

In some cases, the material delivery device may comprise a device selected from the group consisting of: a 3D printer; a layer printing device; an electrospinning device; a melt-spinning device; a melt-electrospinning device; a misting assembly; a sprayer; an electrosprayer; a fused deposition device; a selective laser sintering device; a fiber dispenser; a wire dispenser; a thread dispenser; a resin deposition device, such as a UV-curable resin deposition device; a stereolithography device; a phase separation device; a wet spinning device; a dip coating device; a lathe; a milling machine; a chemical etching device; a plasma etching device; a negative mold-over device; an injection molding device; and any combination thereof. The material delivery device can comprise two or more devices selected from the group consisting of: a 3D printer; a layer printing device; an electrospinning device; a melt-spinning device; a melt-electrospinning device; a misting assembly; a sprayer; an electrosprayer; a fused deposition device; a selective laser sintering device; a fiber dispenser; a wire dispenser; a thread dispenser; a resin deposition device, such as a UV-curable resin deposition device; a stereolithography device; a phase separation device; a wet spinning device; a dip coating device; a lathe; a milling machine; a chemical etching device; a plasma etching device; a negative mold-over device; an injection molding device; and any combination thereof.

In some cases, the material may comprise one or more materials selected from the group consisting of: synthetic polymer; natural polymer; protein; metal; metal alloy; collagen; elastin; a glycosaminoglycan (e.g. heparin, heparan sulfate, chondroitin sulfate, dermatan sulfate, keratan sulfate, and/or hyaluronic acid); a proteoglycan (e.g. decorin, biglycan, testican, bikunin, fibromodulin, lumican, versican, perlecan, neurocan, aggrecan and/or brevican); an alginate; cellulose; gelatin; silk fibroin; fibrinogen; chitosan; an enzyme; fibronectin; glycerin; integrin; keratin; a vitamin; a carbohydrate; a monosaccharide; a disaccharide; a polysaccharide; a nucleoside; abductin; lignin; a glycolipid; a phospholipid; a sterol; shrilk; cobalt-chrome; nitinol; aluminum oxide; magnesium; iron; zinc; steel; titanium; vitalium; alacrite; platinum; gold; silver; copper; manganese; a polyester; a polyurethane; a polycarbonate; a polyether; a polysulfone; a polyamide; a polyetheramide; a polystyrene; a polybutadiene; a polyisoprene; a poly(methyl methacrylate); a polyanhydride; a polydimethylsiloxane; a polydioxanone; polyethylene; glycol; polyethylene terephthalate; a polyglycolide; a polyhydroxyalkanoate; polyimide; polytetrafluoroethylene; polyvinylidene fluoride; polyethylene; polypropylene; polyvinylfluoride; polyvinylchloride; polyacylonitrile; silicone; a ceramic; a bioceramic; a bioglass; a composite material; and any combination thereof.

In some cases, the 3D covering may comprise varied properties along its length. The 3D covering can comprise at least one customized portion. In some cases, the 3D covering may comprise at least a portion with a thickness from about 10 micrometers (μm) to about 1 centimeter (cm). The 3D covering can comprise at least a portion with a thickness from about 50 μm to about 500 The 3D covering can comprise at least a portion with a thickness from about 200 μm to about 300 μm.

In some cases, the 3D covering may comprise at least a portion with a bulk porosity less than about 99%. The 3D covering can comprise at least a portion with a bulk porosity from about 1% to about 90%. The 3D covering can comprise at least a portion with a bulk porosity from about 10% to about 80%. The 3D covering can comprise at least a portion with a bulk porosity from about 30% to about 80%. The 3D covering can comprise at least a portion with a bulk porosity from about 50% to about 70%.

In some cases, the 3D covering may comprise a length from about 1 millimeter (mm) to about 1 meter (m). The 3D covering can comprise a length from about 3 cm to about 50 cm. The 3D covering can comprise a length from about 20 cm to about 30 cm.

In some cases, the 3D covering may comprise at least a portion with a compliance under a physiologic load that is less than about 99%. The 3D covering can comprise at least a portion with a compliance under a physiologic load that is from about 1% to about 50%. The 3D covering can comprise at least a portion with a compliance under a physiologic load that may be from about 10% to about 25%.

In some cases, the 3D covering may comprise at least a portion with an ultimate strength from about 0.1 megapascal (MPa) to about 500 MPa. The 3D covering can comprise at least a portion with an ultimate strength from about 0.5 MPa to about 100 MPa. The 3D covering can comprise at least a portion with an ultimate strength from about 1 MPa to about 10 MPa.

In some cases, the 3D covering may comprise at least a portion with a biodurability from about 1 hour to about 10 years. The 3D covering can comprise at least a portion with a biodurability from about 48 hours to about 2 years. The 3D covering can comprise at least a portion with a biodurability from about 3 months to about 6 months.

In some cases, the 3D covering may comprise a drug, and the 3D covering can be configured to release the drug for a duration from about 1 hour to about 10 years. The 3D covering can be configured to release the drug for a duration from about 48 hours to about 2 years. The 3D covering can be configured to release the drug for a duration from about 3 months to about 6 months.

In some cases, the 3D covering may comprise at least a portion with a macropore size from about 10 µm to about 1000 µm. The 3D covering can comprise at least a portion with a macropore size from about 20 µm to about 200 µm. The 3D covering can comprise at least a portion with a macropore size from about 50 µm to about 100 µm.

In some cases, the 3D covering may comprise at least a portion with a macropore spacing from about 10 µm to about 1000 µm. The 3D covering can comprise at least a portion with a macropore spacing from about 100 µm to about 500 µm. The 3D covering can comprise at least a portion with a macropore spacing from about 200 µm to about 400 µm.

In some cases, the 3D covering may comprise at least a portion with a water permeability of less than about 300 milliliter per centimeter squared per minute (ml/cm2/min). The 3D covering can comprise at least a portion with a water permeability from about 50 ml/cm2/min to about 200 ml/cm2/min. The 3D covering can comprise at least a portion with a water permeability from about 100 ml/cm2/min to about 150 ml/cm2/min.

In some cases, the 3D covering may comprise a texture with from about 0.25 nanometer (nm) to about 50 µm roughness value Ra. The 3D covering can comprise a texture with from about 0.2 µm to about 12.5 µm roughness value Ra.

The 3D covering can comprise a texture with from about 1.6 µm to about 6.3 µm roughness value Ra.

In some cases, the 3D covering may comprise a suture retention strength up to about 1 kilogram-force (Kgf). The 3D covering can comprise a suture retention strength of from about 50 gram-force (gf) to about 500 gf. The 3D covering can comprise a suture retention strength of between 100 gf and 200 gf.

In some cases, the 3D covering may comprise at least a portion with a kink radius of up to about 1 meter (m). The 3D covering can comprise at least a portion with a kink radius of from about 5 mm to about 100 mm. The 3D covering can comprise at least a portion with a kink radius of from about 10 mm to about 20 mm.

In some cases, the 3D covering may comprise fibers with a width and/or diameter from about 10 µm to about 1 mm. The 3D covering can comprise fibers with a width and/or diameter from about 20 µm to about 500 µm. The 3D covering can comprise fibers with a width and/or diameter from about 50 µm to about 100 µm.

In some cases, at least a portion of the 3D covering may comprise a greater axial compliance than radial compliance. The at least a portion of the 3D covering can comprise a majority of fibers that are circumferentially oriented.

In some cases, at least a portion of the 3D covering may comprise an axial compliance that is relatively equal to its radial compliance. The at least a portion of the 3D covering can comprise a majority of fibers that are anisotropically oriented.

In some cases, the 3D covering may comprise a material selected from the group consisting of: fiber reinforced material; particle reinforced material; flake reinforced material; a multi-layered material; a segmented material; and any combination thereof.

In some cases, the system may comprise a user interface. The system can be configured to display an image of the tubular conduit on the user interface. The displayed image can be a 3D image. The system can be configured to allow a user to modify the displayed image. The system can be configured to display an image of a proposed 3D covering. The displayed image can be a 3D image. The system can be configured to allow a user to modify the displayed image. The user interface can comprise a user control comprising an electronic model modifying tool. The tool can be configured to modify a model of the tubular conduit. The tool can be configured to modify a model of a proposed 3D covering. The tool can comprise a property modifying function selected from the group consisting of: smooth; erase; spline; fillet, fill; insert a building block; and any combination thereof. The tool can comprise a property modifying function including inserting a building block, the building block comprising an electronic model selected from the group consisting of: anastomosis; dimple; reinforcing spline; and any combination thereof. The tool can be configured to measure distance. The construction signal can be based on information provided by a user of the system via the user interface.

In some cases, the material delivery device may comprise a modification assembly configured to modify at least one of the 3D covering or the tubular conduit. The modification assembly can be configured to deliver energy to at least one of the 3D covering or the tubular conduit. The energy can comprise heat and/or cooling. The modification assembly can be configured to deliver a second material to at least one of the 3D covering or the tubular conduit. The second material can comprise a material selected from the group consisting of: solvent; drug; agent; and any combination thereof. The modification assembly can be configured to deliver moisture to at least one of the 3D covering or the tubular conduit.

In some cases, the system may comprise a target onto which the material is delivered. The target can comprise a mandrel configured to rotate. The material delivery device can be constructed and arranged to produce the target. The target can comprise a disposable component.

In some cases, the system may comprise a sterile barrier constructed and arranged to maintain sterility between the material delivery device and one or more other portions of the system.

According to another aspect of the present disclosure, a graft device may be produced by a system as described herein. The graft device may comprise a tubular conduit and a 3D covering surrounding the tubular conduit, and the 3D covering may be produced by a material delivery device of the system. The material delivery device may produce the 3D covering based on image data of the tubular conduit. The tubular conduit can comprise a discrete feature, and the 3D covering can comprise at least one customized portion positioned relative to the discrete feature.

According to another aspect of the present disclosure, a method of producing a graft device uses a system as described herein. The method may comprise (1) producing image data of a tubular conduit, (2) receiving the image data of the tubular conduit and creating an electronic model of the tubular conduit, (3) creating an electronic model of a 3D covering and (4) delivering material to produce a 3D covering. The method can comprise modifying the electronic model of the tubular conduit produced in (2). The system can comprise modifying the electronic model of the 3D covering produced in (3). The method 3D covering produced in (4) can be produced by delivering the material onto the tubular conduit (e.g. directly onto the tubular conduit). The method can comprise a (5) including placing the 3D covering about the tubular conduit.

The technology described herein, along with the attributes and attendant advantages thereof, may best be appreciated and understood in view of the following detailed description taken in conjunction with the accompanying drawings in which representative embodiments are described by way of example.

DETAILED DESCRIPTION

Figure 1:
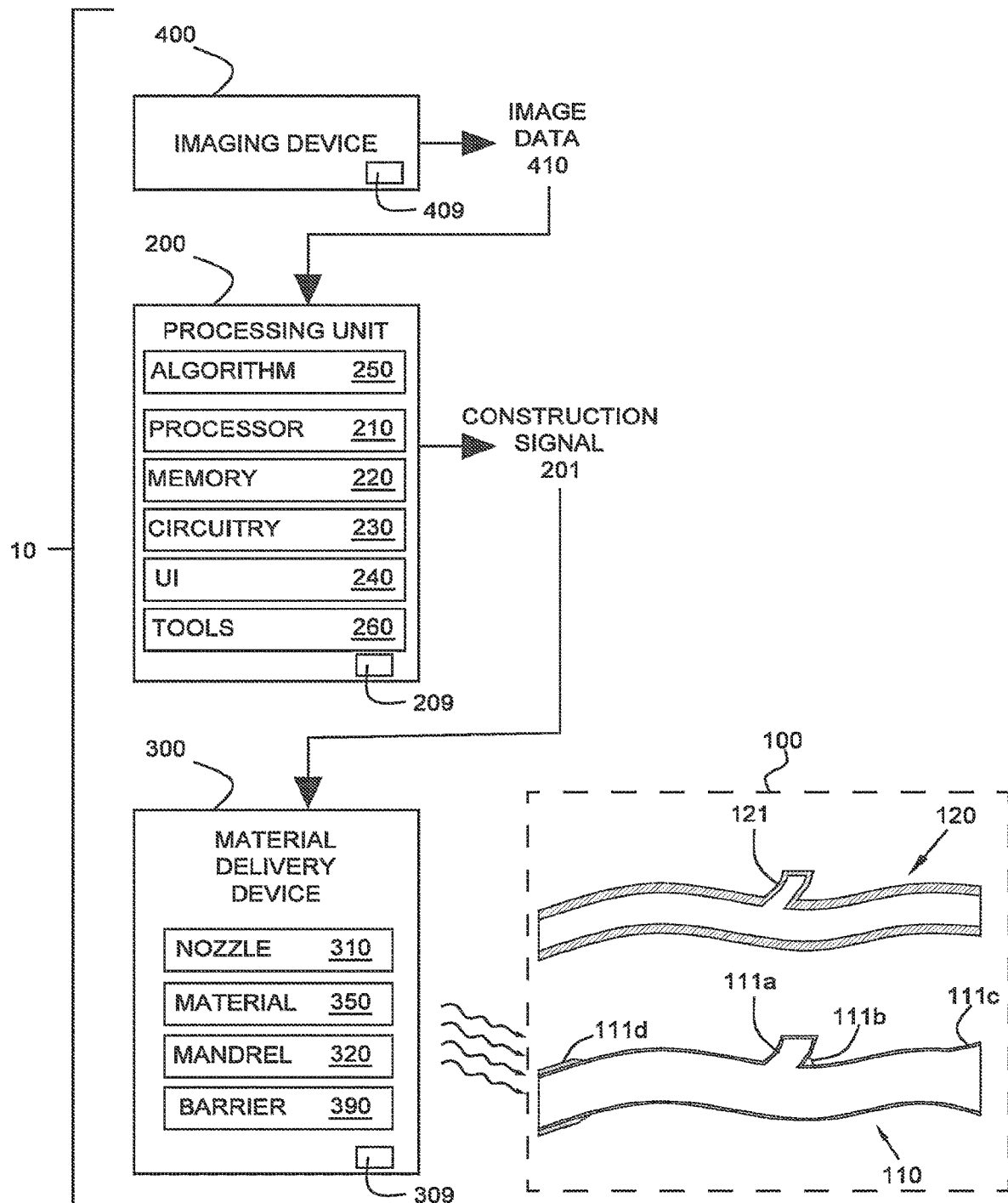
FIG. 1 illustrates a schematic view of a system for producing a graft device.

Reference will now be made in detail to the present embodiments of the technology, examples of which are illustrated in the accompanying drawings. The same reference numbers are used throughout the drawings to refer to the same or like parts.

It may be further understood that the words "comprising" (and any form of comprising, such as "comprise" and "comprises")), "having" (and any form of having, such as "have" and "has"), "including" (and any form of including, such as "includes" and "include") or "containing" (and any form of containing, such as "contains" and "contain") when used herein; specify the presence of stated features, integers, steps, operations, elements, and/or components, but may not preclude the presence or addition of one or more other features, integers, steps, operations, elements, components, and/or groups thereof.

As used herein; the term "about" may mean the referenced numeric indication plus or minus 15% of that referenced numeric indication.

It may be understood that, although the terms first, second, third etc. may be used herein to describe various limitations, elements, components, regions, layers and/or sections, these limitations, elements, components, regions, layers and/or sections may not be limited by these terms. These terms may only be used to distinguish one limitation, element, component, region, layer or section from another limitation, element, component, region, layer or section. Thus, a first limitation, element, component, region, layer or section discussed below may be termed a second limitation, element, component, region, layer or section without departing from the teachings of the present application.

It may be further understood that when an element may be referred to as being "on" "attached", "connected" or "coupled" to another element, it can be directly on or above, or connected or coupled to, the other element, or one or more intervening elements can be present. In contrast, when an dement may be referred to as being "directly on". "directly attached", "directly connected" or "directly coupled" to another element, there may be no intervening elements present. Other words used to describe the relationship between elements may be interpreted in a like fashion (e.g. "between" versus "directly between," "adjacent" versus "directly adjacent," etc.).

It may be further understood that when a first element may be referred to as being "in", "on" and/or "within" a second element, the first element can be positioned: within an internal space of the second element, within a portion of the second element (e.g. within a wall of the second element); positioned on an external and/or internal surface of the second element; and any combination thereof.

As used herein, the term "proximate" may generally refer to locations relatively close to, on, in and/or within a referenced component or other location.

Spatially relative terms, such as "beneath," "below," "lower," "above," "upper" and the like may generally refer to an element and/or feature's relationship to another element(s) and/or feature(s) as, for example, illustrated in the figures. It may be understood that the spatially relative terms may be intended to encompass different orientations of the device in use and/or operation in addition to the orientation depicted in the figures. For example, if the device in a figure may be turned over, elements described as "below" and/or "beneath" other elements or features may then be oriented "above" the other elements or features. The device can be otherwise oriented (e.g. rotated about 90 degrees or at other orientations) and the spatially relative descriptors used herein interpreted accordingly.

As described herein, "room pressure" may generally refer to a pressure of the environment surrounding the systems and devices as described herein. Positive pressure may include pressure above room pressure or simply a pressure that may be greater than another pressure, such as a positive differential pressure across a fluid pathway component such as a valve. Negative pressure may include pressure below room pressure or a pressure that may be less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described herein.

The term "diameter" may generally refer to a non-circular geometry and in some cases may be taken as the diameter of a hypothetical circle approximating the geometry being described. For example, when describing a cross section, such as the cross section of a component, the term "diameter" may be taken to represent the diameter of a hypothetical circle with the same cross sectional area as the cross section of the component being described.

The terms "major axis" and "minor axis" of a component may generally refer to the length and diameter, respectively, of the smallest volume hypothetical cylinder which can completely surround the component.

The terms "reduce", "reducing", "reduction" and the like, may generally refer to a reduction in a quantity, including a reduction to zero. Reducing the likelihood of an occurrence may include prevention of the occurrence.

The term "and/or" where used herein may be taken as specific disclosure of each of the two specified features or components with or without the other. For example "A and/or B" may be to be taken as specific disclosure of each of (i) A, (ii) B and (iii) A and B, just as if each may be set out individually herein.

The term "biodurability" may in some cases generally refer to a preservation of one or more physical properties, one or more mechanical properties, one or more chemical properties, or any combination thereof during an exposure to a biological environment or a biologically similar environment over a period of time. In some cases, a period of time may comprise an extended period of time. In some cases, a period of time may comprise about 1 month, about 6 months, about 1 year, about 2 years, about 5 years, about 10 years or more. A biological environment may comprise a surface of a subject. A biological environment may comprise an internal surface or internal volume of a subject. A biologically similar environment may comprise an artificial setting such as a media solution or incubator environment that simulates a biological environment.

The term "bulk porosity" may in some cases generally refer to a bulk porosity of a material or structure, such as a processed material or structure. A bulk porosity may be equivalent to $1-W/(\mu V)$ where W equals a weight of a material or structure, $\mu$ may be the weight per unit volume of a material or structure prior to a processing, and V may be the volume of the material or structure, such as the processed material or structure.

The term "macropore" may in some cases generally refer to a lumen through a wall of a structure (such as a matrix) having a cross sectional area of at least about 3E-4 millimeters squared ($mm^2$), at least about 3E-3 $mm^2$, or at least about 1E-2 $mm^2$.

The term "kink radius" may in some cases generally refer to an inner radius of a structure (such as a tube) measured when the structure may be bent to a limit before buckling may occur.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it may be appreciated that all features set out in any of the claims (whether independent or dependent) can be combined in any given way.

Provided herein are medical devices for implantation in a mammalian patient, as well as systems, devices and methods for producing these medical devices. The medical devices can comprise graft devices that are implanted to carry fluids (e.g. blood or other body fluid) from a first anatomical location to a second anatomical location of the patient. The graft devices may include a conduit or other implantable structure ("conduit" herein), such as a harvested blood vessel segment or other tubular conduit, other harvested tissue and/or an artificial conduit, and a three-dimensional (3D) covering that surrounds the conduit. The systems can comprise a material delivery device configured to produce the 3D covering (e.g. directly onto the conduit or fabricated separately for subsequent placement about the conduit). The systems described herein can include a processing unit that receives image data related to the patient's anatomy, such as image data related to an organ or other tissue. In some cases, the image data may be related to a tubular conduit or other tissue of a patient (e.g data from one or more images of an in-vivo tubular tissue conduit and/or from images of an already harvested tubular tissue conduit). The processing unit can produce a construction signal based on the image data, the construction signal used by the material delivery device to produce the 3D covering.

Referring now to FIG. 1, a system for creating an implantable device for a patient is illustrated. System 10 may comprise processing unit 200 and a material delivery device (MDD) 300. System 10 may be constructed and arranged to produce an implantable device, such as graft device 100 which may comprise a three-dimensional (3D) covering, covering 110, which can be positioned about an implantable structure, conduit 120, such as a tubular conduit or other implantable structure. System 10 can comprise an imaging device, such as imager 400 shown, which produces image data 410. Image data 410 can represent information related to conduit 120 and/or a portion of a patient's anatomy (e.g. a portion of the patient's cardiovascular system).

Processing unit 200 may be configured to receive image data 410 from imager 400. Imager 400 can comprise an imaging device selected from the group consisting of: CT imager, OCT imager; MRI, 3D Scanner, camera; infrared camera; ultrasound imager; laser-scanning device, and any combination thereof. Imager 400 can produce image data 410 (e.g. image data of conduit 120 and/or any portion of the patient's anatomy), and processing unit 200 can receive the image data 410 from imager 400.

Image data 410 can be collected from an in-situ conduit 120 (e.g. a vein, artery or other blood vessel, prior to being harvested) and/or after conduit 120 has been harvested from the patient. In some cases, image data 410 may comprise data collected both prior to and after a conduit 120 has been harvested from the patient. Image data 410 can comprise various geometric and other information of conduit 120, such as data selected from the group consisting of: surface topography data, surface geometry data; periphery data; length data, diameter data, thickness data such as wall thickness data; taper data; eccentricity data; relative position data; trajectory data; speed of motion data; relative angle data; radiopacity data; blood flow data; echographic data; spectroscopic data; and any combination thereof. Image data 410 can comprise data related to one or more abnormalities or other particular, relatively discrete, features of conduit 120, feature 121. In the embodiment shown in FIG. 1, conduit 120 may comprise feature 121 comprising a sidebranch. In some cases, feature 121 of conduit 120 can comprise one or more discrete features selected from the group consisting of: sidebranch; recess; projection; end; end portion; bend portion (e.g. a region of bending); lobe; bifurcation; trifurcation; a dilated portion; a swollen portion; valve; a tapered portion; a location of a surgical staple; an angled portion; a calcified tissue portion; an atheromatous tissue portion; a partially occluded portion; a fully occluded portion; and any combination thereof. In some cases, image data 410 can comprise sidebranch data selected from the group consisting of: location; diameter; taper angle; and any combination thereof one or more sidebranches of conduit 120 may include a ligation device (e.g. suture or a ligation clip placed after harvest of conduit 120), and image data 410 can include information related to the position of the ligation device, ligation device geometry and/or ligation device type.

Processing unit 200 can comprise one or more algorithms, algorithm 250. Processing unit 200 can be configured to receive, process (e.g. mathematically process), store and/or transmit data. Processing unit 200 can be configured to receive image data 410 from imaging device 400, and algorithm 250 can be configured to process the received image data 410 to produce a construction signal, construction signal 201. Construction signal 201 can comprise geometry and other construction information used by material delivery device (MDD) 300 to produce covering 110. Construction signal 201 can be based on one or more properties of conduit 120 (e.g. as determined by algorithm 250). Construction signal 201 can be configured to produce a covering 110 that has varied properties along the length of covering 110, such as to provide mechanical support for conduit 120 at one or more particular locations MDD 300 can receive construction signal 201 from processing unit 200, and deliver one or more materials, material 350, to produce covering 110 based on construction signal 201. In some cases, MDD 300 may deliver material 350 directly onto conduit 120 while producing covering 110 in some cases, covering 110 may be positioned about conduit 120 after covering 110 is produced by MDD 300.

Conduit 120 can comprise living tissue (including previously harvested tissue), such as one or more segments of tissue selected from the group consisting of: cylindrical tissue; organ tissue; saphenous vein; vein; artery; urethra; intestine; esophagus; ureter; trachea; bronchi; duct; fallopian tube; and any combination thereof. In some cases, conduit 120 can comprise an artificial material (e.g. a plastic or other non-tissue tube or other structure) In some cases, conduit 120 may comprise a first length of tissue that may be subsequently shortened (e.g. one or more ends cut off) during the creation of graft device 100. In some cases, conduit 120 may comprise a single lumen structure of tissue. In some cases, conduit 120 may comprise a tubular structure including at least a bifurcation or trifurcation of lumens. In some cases, conduit 120 may comprise bone, ligament and/or tendon tissue. Conduit 120 can comprise one or more discrete features 121 as described above, such as a discrete feature 121 that may be identified by algorithm 250 (e.g. identified by analyzing image data 410).

Graft device 100 can be used as an arterial bypass graft, such as to be used as a coronary artery bypass graft. In some cases, graft device 100 may be configured for use as a dialysis graft. In some cases, graft device 100 may comprise one or more graft devices configured to be used as graft selected from the group consisting of artery bypass graft; coronary artery bypass graft; dialysis graft; peripheral arterial bypass graft; great vessel replacement, great vessel bypass graft; esophageal graft; tracheal graft; bronchial graft; biliary duct graft; intestinal graft; organ transplant vascular connection graft; neuronal replacement implant; ligament graft; ligament replacement; tendon graft; tendon replacement; transplant organ coating; fallopian tube; urethra; ureter; cartilage; hip joint; shoulder joint; intervertebral disc; menisci; and any combination thereof.

As described herein, covering 110 may include varied properties along its length, such as when covering 110 comprises one or more customized portions 111. In some cases, one or more customized portions 111 may be provided based on image data 410 (e.g. as determined by algorithm 250). In some cases, one or more customized portions 111 may be included proximate one or more discrete features 121.

In some cases, covering 110 and/or one or more customized portions 111 may comprise a parameter with a value selected from Range 1, Range 2 and/or Range 3 of Table 1 below. Note that the value of one parameter from one range may not necessarily be linked to the same range of a different parameter.

TABLE 1

| Feature | Range 1 | Range 2 | Range 3 |
| --- | --- | --- | --- |
| Thickness | 10 µm to 1 cm | 50 µm to 500 µm | 200 µm to 300 µm |
| Bulk Porosity | 0% to 99% | 30% to 80% | 50% to 70% |
| Length | 1 mm to 1 m | 3 cm to 50 cm | 20 cm to 30 cm |
| Conformality of covering 110 to conduit 120 | Constrictive to loose fitting - entire length or local portion thereof | Restrictive to loose fitting - entire length or local portion thereof | Restrictive - entire length or local portion thereof |
| Compliance under a physiologic load such as arterial pressure | 0% to 99% | 1% to 50% | 10% to 25% |
| Ultimate Strength | 0.1 MPa to 500 MPa | 0.5 MPa to 100 MPa | 1 MPa to 10 MPa |
| Biodurability | 1 hour to 10 years | 48 hours to 2 years | 3 months to 6 months |
| Drug release duration (i.e. when impregnated with a drug or other agent) | 1 hour to 10 years | 48 hours to 2 years | 3 months to 6 months |
| Macropores | | | |
| (1) Size | (1) 10 µm to 1000 µm | (1) 20 µm to 200 µm | (1) 50 µm to 100 µm |
| (2) Spacing | (2) 10 µm to 1000 µm | (2) 100 µm to 500 µm | (2) 200 µm to 400 µm |
| Water Penneability | 0 mL/cm$^2$/min to | 50 mL/cm$^2$/min to | 100 mL/cm$^2$/min to |

TABLE 1-continued

| Feature | Range 1 | Range 2 | Range 3 |
|---|---|---|---|
| | 300 mL/cm²/min | 200 mL/cm²/min | 150 mL/cm²/min |
| Texture (Roughness values Ra) | 0.025 nm to 50 µm | 0.2 µm to 12.5 µm | 1.6 µm to 6.3 µm |
| Suture retention strength | 0 gf to 1 Kgf | 50 gf to 500 gf | 100 gf to 200 gf |
| Kink resistance (kink radius) | 0 mm to 1 m | 5 mm to 100 mm | 10 mm to 20 mm |
| Fiber width and/or diameter | 10 µm to 1 mm | 20 µm to 500 µm | 50 µm to 100 µm |

Figure 1A:
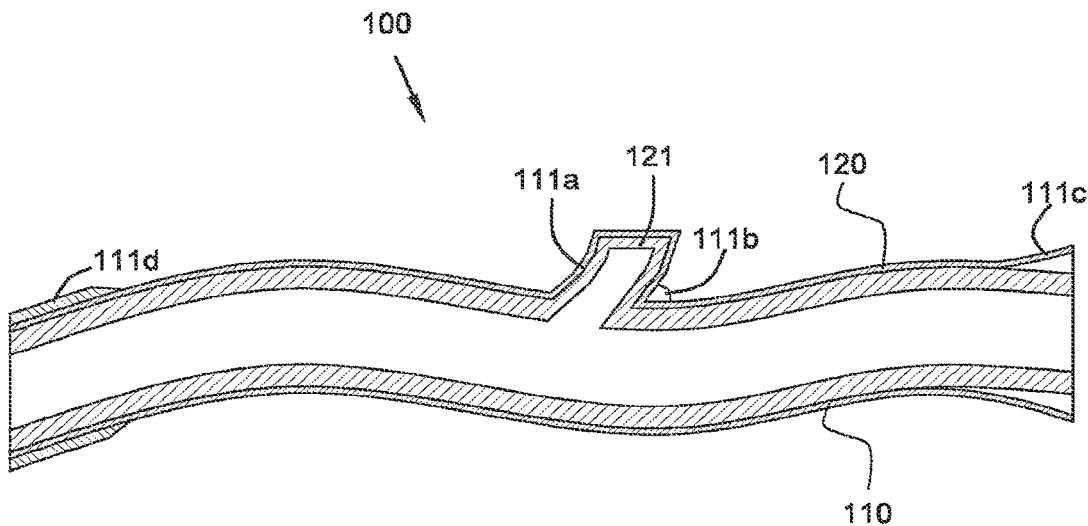
FIG. 1A illustrates a side sectional view of a graft device comprising a covering including multiple customized portions.
Figure 1B:
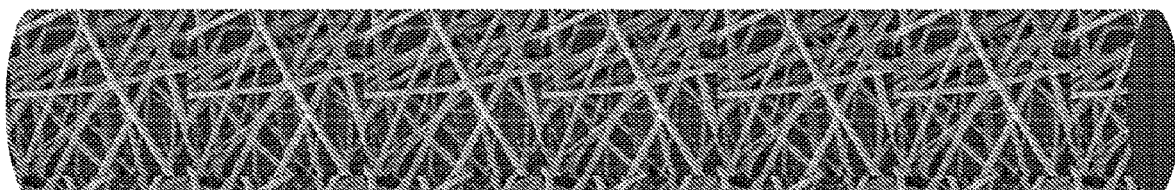
FIG. 1B illustrates a side sectional view of a graft device comprising a covering including a large proportion of isotropically oriented fibers.
Figure 1C:
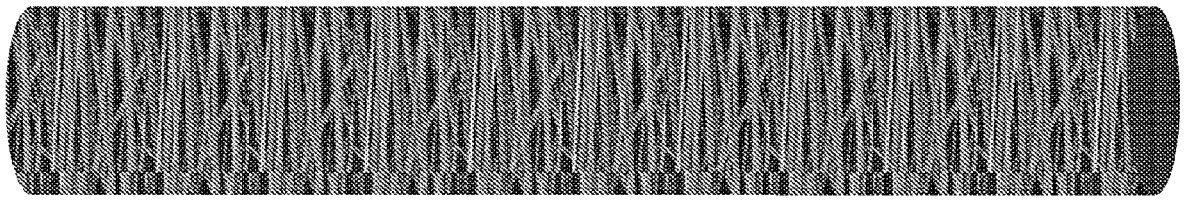
FIG. 1C illustrates a side sectional view of a graft device comprising a covering including a large proportion of circumferentially oriented fibers.

In some cases, covering 110 can comprise a compliance, C, that may be equal (e.g. relatively equal) in both axial and tangential directions ($C_{axial}=C_{tangential}$), such as is described herein in reference to FIG. 1C. In some cases, covering 110 can comprise different axial compliance than its circumferential (i.e. tangential) compliance, such as when covering 110 may comprise high circumferential compliance and low axial compliance ($C_{axial}<C_{tangential}$), or when covering 110 may comprise high axial compliance and low circumferential compliance ($C_{axial}>C_{tangential}$), such as is described herein in reference to FIG. 1C. In some cases, covering 110 may comprise homogeneous materials, such as materials including homopolymers, copolymers, pure metals and/or metal alloys. In some cases, covering 110 may comprise composite materials, such as fiber reinforced, particle reinforced, flake reinforced, multi-layered, and/or segmented materials.

In some cases, material delivery device (MDD) 300 may comprise a device configured to produce covering 110 by delivering material 350 using an additive printing process, such as a process similar to that performed by commercially available 3D printers. In some cases, MDD 300 may deliver material 350 in a series of layers to produce covering 110. In some cases, MDD 300 may deliver material 350 as a fiber. In some cases, MDD 300 may deliver material 350 onto a surface, such as mandrel 320 shown, to produce covering 110, after which covering 110 may be positioned about conduit 120. In some cases, MDD 300 may produce covering 110 by delivery of material 350 directly onto conduit 120 (e.g. while mandrel 320 may be positioned within conduit 120). In some cases, a first portion of covering 110 may be produced by delivery of material 350 onto conduit 120, and a second portion of covering 110 may be produced by delivery of material 350 onto a surface (e.g. mandrel 320). In some cases, the second portion of covering 110 can subsequently be positioned about conduit 120 and/or the first portion of covering 110.

In some cases, MDD 300 may comprise a device configured to also produce a target (e.g. a template used to produce covering 110), such as when MDD 300 may create mandrel 320. The outer geometry of mandrel 320 may define the inner surface geometry of covering 110, and MDD 300 can be configured to produce a customized mandrel 320, such as to create a covering 110 comprising one or more customized portions 111. In some cases, mandrel 320 may be disposed of after the creation of covering 110. In some cases, mandrel 320 can be used to create multiple coverings 110.

In some cases, MDD 300 may comprise one, two or more devices selected from the group consisting of: a 3D printer; a layer printing device; an electrospinning device, a melt-spinning device, a melt-electrospinning device, a misting assembly; a sprayer; an electrosprayer, a fused deposition device; a selective laser sintering device; a fiber dispenser; a wire dispenser; a thread dispenser; a resin deposition device, such as a UV-curable resin deposition device; a stereolithography device; a phase separation device; a wet spinning device, a dip coating device; a lathe; a milling machine; a chemical etching device; a plasma etching device; a negative mold-over device; an injection molding device; and any combination thereof. In some cases, MDD 300 and/or other components of system 10 may be constructed and arranged as described herein in reference to FIG. 3. For example, MDD 300 can comprise a modification assembly, such as modification assembly 605 described herein in reference to FIG. 3, such as to apply or otherwise direct toward covering 110, conduit 120 and/or mandrel 320 energy or material selected from the group consisting of: light; heat; cooling; moisture; solvent, drug or other agent, and any combination thereof.

Material delivery device (MDD) 300 can comprise one, two or more nozzles or other material delivery elements, nozzle 310. MDD 300 can be configured to translate, rotate and/or otherwise reposition nozzle 310 along a pathway. Nozzle 310 can comprise two or more concentric nozzles. MDD 300 can be configured to control the delivery of material through the one or more nozzles 310, such as to control the speed of material 350 delivered to nozzle 310 and/or control the cross sectional shape and/or area of nozzle 310.

Material 350 may comprise one or more materials configured for implantation in a patient. Material 350 can comprise one, two or more materials selected from the group consisting of synthetic polymer; natural polymer; protein, metal; metal alloy; collagen; elastin; a glycosaminoglycan (e.g. heparin, heparan sulfate, chondroitin sulfate, dermatan sulfate, keratan sulfate, and/or hyaluronic acid); a proteoglycan (e.g. decorin, biglycan, testican, bikunin, fibromodulin, lumican, versican, perlecan, neurocan, aggrecan and/or brevican); an alginate, cellulose; gelatin; silk fibroin; fibrinogen; chitosan; an enzyme; fibronectin; glycerin; integrin; keratin; a vitamin; a carbohydrate; a monosaccharide; a disaccharide; a polysaccharide; a nucleoside; abductin, lignin; a glycolipid, a phospholipid, a sterol; shrilk; cobalt-chrome; nitinol; aluminum oxide, magnesium; iron, zinc; steel; titanium; vitalium; alacrite; platinum; gold; silver; copper; manganese; a polyester, a polyurethane, a polycarbonate; a polyether; a polysulfone; a polyamide; a polyetheramide; a polystyrene; a polybutadiene; a polyisoprene; a poly(methyl methacrylate); a polyanhydride; a polydimethylsiloxane; a polydioxanone; polyethylene; glycol; polyethylene terephthalate; a polyglycolide; a polyhydroxyalkanoate, polyimide; polytetrafluoroethylene, polyvinylidene fluoride; polyethylene; polypropylene; polyvinylfluoride; polyvinylchloride; polyacylonitrile; silicone; a ceramic; a bioceramic; a bioglass; a composite material and any combination thereof.

As described herein, material delivery device (MDD) 300 can include a mandrel or other target, mandrel 320. In some cases, mandrel 320 may provide a support structure onto which material 350 may be delivered by nozzle 310. In some cases, conduit 120 may be positioned over mandrel 320 and material 350 may be delivered onto conduit 120 while mandrel 320 may be in place. In some cases, mandrel 320 may be configured to rotate, translate and/or otherwise move in relation to nozzle 310 (e.g. via motion of mandrel 320 and/or motion of nozzle 310) In some cases, mandrel 320 may comprise a flat or irregularly shaped surface onto which material 350 may be delivered to produce covering 110. In some cases, MDD 300 may be configured to produce one or more mandrels 320, such as when a subset of mandrels or each mandrel 320 may be disposable (e.g. used for a limited time such as to produce a single covering 110). In some cases, nozzle 310 can comprise a first nozzle 310a which may be used to produce a mandrel 320 and a second nozzle 310b which may be used to apply material 350 onto mandrel 320 to produce covering 110.

In some cases, MDD 300 may comprise a barrier 390, such as a sterile barrier configured to maintain sterility between one or more portions of MDD 300 and one or more sterile components of system 10. Barrier 390 can comprise a sterile drape (e.g. a sterile plastic drape) and/or a molded sterile covering (e.g. a molded plastic covering). In some cases, one or more portions of MDD 300 may be sterile (e.g. sterilizable).

Processing unit 200 can comprise one or more electrical or other components, such as one or more of processor 210, memory 220, circuitry 230 and/or a user interface (UI) 240, all shown. Processing unit 200 can comprise one or more algorithms, algorithm 250. Processor 210 can comprise a microprocessor or other microcontroller configured to perform a series of events (e.g. events whose outcome may be determined by status of a parameter or outcome of a previous event). Memory 220 can comprise volatile or non-volatile electronic memory used to temporarily or permanently store information. In some cases, memory 220 may comprise a library of information. For example, memory 220 can store information selected from the group consisting of: tissue type; material 350 type; information regarding the application (e.g. clinical application) of graft device 100; information regarding use of one or more tools, such as tool 260 described herein; compliance information; density information; strength information; modulus of elasticity information; elastic limit information; wall thickness information; material 350 shrinkage and/or cure time at varying temperature and/or relative humidity; spacing to mandrel 320 or other target; minimum bend radius of covering 110; maximum ovality of covering 110; and any combination thereof. Construction signal 201 can be based, at least partially, on information stored in memory 220. Circuitry 230 may comprise one or more of analog and/or digital electronic componentry common to electromechanical, microprocessor controlled equipment.

UI 240 can comprise one or more user input and/or user output components selected from the group consisting of: switch; keyboard; membrane keypad; knob; lever; touchscreen, light such as an LED; display; audio transducer such as a buzzer or speaker; tactile transducer such as an eccentric rotational element; and any combination thereof. In some cases, UI 240 can comprise a display such that an image (e.g a 2D or 3D image) of all or a portion of conduit 120 can be provided to a user of system 10. In some cases, a user can modify the image of conduit 120, via one or more input components of UI 240. In some cases, UI 240 can display a proposed (e.g. for modification by the user) or actual (i.e. final) image (e.g. a 2D or 3D image) of all or a portion of covering 110. In some cases, construction signal 201 may be at least partially based on information provided by a user via UI 240.

User interface (UI) 240 and/or another component of processing unit 200 or system 10 can comprise one or more tools configured to allow adjustment of a parameter or other information, tool 260 shown. In some cases, tool 260 may be configured to allow a user to modify an electronic model of conduit 120 (e.g. a model displayed on UI 240). In some cases, tool 260 may be configured to allow a user to modify an electronic model of covering 110 (e.g. a proposed or final model of covering 110 that may be displayed on UI 240). In some cases, tool 260 may provide a property modifying function selected from the group consisting of: smooth; erase; spline; fillet, fill, insert a building block (e.g. a geometric structure to the model); and any combination thereof. In some cases, tool 260 may be configured to allow a user to insert a building block comprising an electronic model selected from the group consisting of: anastomosis; dimple (e.g. to accommodate a sidebranch); reinforcing spline, and any combination thereof. In some cases, tool 260 may be configured to measure a distance (e.g. a length, width, diameter, taper, radius of curvature and/or thickness).

In some cases, a user of system 10 may enter information via UI 240, and construction signal 201 may be based at least in part on that information. For example, a user can enter information that creates a customized portion 111 and/or positions a customized portion 111 along covering 110. In some cases, algorithm 250 may produce a construction signal 201 that may be based both on image data 410 and information provided by a user via UI 240.

Algorithm 250 can be configured to analyze one or more portions of image data 410 and may produce construction signal 201 based on the analysis. The analysis of image data 410 by algorithm 250 can include analysis of other information, such as information stored in memory 220 and/or information provided by a user via user interface (UI) 240. Using image data 410 and/or such other information, algorithm 250 can produce mathematical models, geometric models, thresholds, boundary conditions and other information relevant to the creation of construction signal 201. In some cases, construction signal 201 may be based on both image data 410 and other information, such as information stored in memory 220 and/or information input by a user of system 10 via UI 240. In some cases, algorithm 250 may be configured to produce a spatial model and/or other three-dimensional model of conduit 120 based on image data 410 (e.g. image data including multiple slices of a CT image or other multi-dimensional information produced by imaging device 400). In some cases, a user of system 10 can modify the three-dimensional model of conduit 120, such as by using one or more controls or tools of UI 240.

In some cases, algorithm 250 may be configured to produce a point cloud, surface model and/or other three-dimensional model of a "proposed" covering 110, such as to enable one or more modifications of the model to be made prior to producing a construction signal 201 used to produce covering 110 for graft device 100. The one or more modifications of the model can be performed automatically by algorithm 250 (e.g. based on one or more identified discrete features 121 of conduit 120) and/or manually by a user of system 10 (e.g. based on user input). In some cases, algorithm 250 may be configured to produce a model of a covering 110 (proposed and/or final), based on one or more boundary conditions (e.g to optimize hemodynamics by reducing flow turbulence, controlling bending radius, controlling lumen geometry; controlling a transition; controlling a taper; controlling a bend portion; controlling tortuosity; controlling wall shear; preventing buckling, optimizing wall shear stress, modifying an end portion to optimize an anastomotic connection; and/or reducing geometric mismatch near an anastomotic connection). In some cases, algorithm 250 may be configured to convert data from an imaging coordinate system (e.g. coordinate system of imaging device 400 and/or image data 410) to data in a material deposition coordinate system (e.g. a coordinate system of MDD 300). In some cases, the imaging coordinate system may comprise a Cartesian coordinate system and the material deposition coordinate system may comprise a cylindrical, spherical and/or curvilinear coordinate system.

In some cases, algorithm 250 may be configured to identify a feature of conduit 120, such as feature 121 described herein. Algorithm 250 can be configured to create (e.g via construction signal 201) a customized portion 111 of covering 110, the customized portion 111 surrounding or at least proximate that particular feature 121 of conduit 120. A subset of customized portions or each customized portion 111 can comprise a property that is different than another portion of covering 110 (e.g. different than the majority of covering 110). Customized portion 111 can comprise one, two or more portions that have a differentiating property selected from the group consisting of: different (e.g. increased and/or decreased) thickness; different material, different porosity; different pore size, different compliance in one or more directions (e.g. axially and/or radially); different level of conformality; different texture; different alignment and/or orientation of material (e.g. fiber deposition); different stiffness; different fiber diameter; addition of a kink-resisting element; addition of an agent such as a growth factor or pharmaceutical agent; and any combination thereof.

In some cases, covering 110 may comprise one or more customized portions 111 which may be customized to cover a protrusion (e.g a sidebranch or other protrusion) of conduit 120 and/or a ligation device may be used to occlude a sidebranch of conduit 120, such as sidebranch-accommodating portion 111 a shown. Portion 111 a can have a geometry configured to accommodate the sidebranch and/or a ligation device without compromising an internal lumen of conduit 120, such as by creating a space (e.g. a recess or hole in covering 110) in which the sidebranch and/or ligation device may be located. In some cases, one or more customized portions 111 positioned proximate a sidebranch can comprise one or more of: a portion comprising a change (e.g. an increase) in deposition of material 350 such as to mechanically reinforce and/or provide a strain relief at a sidebranch location; a portion configured to constrain a sidebranch such as to minimize hemodynamic disruption in a lumen of conduit 120 (e.g. to cause a slightly greater restriction around bulbous sidebranches or varicosity to force more material towards the lumen and reduce irregularities within the lumen); and any combination thereof. In some cases, a customized portion 111 can include at least a portion that is positioned away from but proximate a sidebranch location, such as a portion of conduit 120 that may include a void region (e.g. a hole and/or recess), such as when algorithm 250 produces a construction signal 201 that may include a customized portion 111 that fills the void proximate the sidebranch.

In some cases, covering 110 may comprise one or more customized portions 111 which comprise a fillet (i.e. rounded interior corner) of covering 110, such as fillet portion 111 b shown and positioned in covering 110 to be located proximate a sidebranch location of conduit 120 when covering 110 may be positioned about conduit 120.

In some cases, covering 110 may comprise one or more customized portions 111 which may be positioned proximate to (e.g. on or near), or otherwise positioned relative to, a discrete feature 121 comprising an end of covering 110, such as a customized portion 111 to be positioned proximate an end of conduit 120 when covering 110 may be positioned about conduit 120. For example, customized portion 111 can comprise a tapered portion of covering 110, such as tapered portion 111 c shown. Tapered portion 111 c can be positioned at one or more ends of covering 110, such as to create a non-conforming portion of customized portion 111 (e.g a space exists between covering 110 and conduit 120 at tapered portion 111 c, such as to allow for radial expansion of conduit 120 at that location). In some cases, customized portion 111 can comprise a reinforced portion (e.g a thicker portion or a portion including more durable materials), such as reinforced portion 111 d shown Reinforced portion 111 d can be positioned at one or more ends of covering 110, and can be combined with tapered portion 111 c at either or both ends. In some cases, one or more reinforced portions 111 d may be positioned about a mid-portion of covering 110, or at any feature 121 of conduit 120, such as when a reinforced portion 111 d may be positioned at a thin-walled portion of conduit 120. In some cases, a customized portion 111 to be located proximate an end of conduit 120 can be optimized for an anastomotic connection, such as to include an optimized shape (e.g. optimized shape for an anastomosis), optimized structural support, optimized material, optimized permeability, optimized porosity, optimized thickness, optimized biodurability, inclusion of agents such as growth factors or pharmaceutical drugs to be delivered to anastomosis and/or other optimized characteristic for performing and maintaining an anastomotic connection. In some cases, conduit 120 and its associated covering 110 may comprise three or more ends, such as when a bifurcated, trifurcated or other multiple branched graft device may be being constructed. One of more ends, such as each end (such as each of three or more ends) can include a customized portion 111 as described herein. In some cases, tapered portion 111 c, reinforced portion 111 d and/or another customized portion 111 can be configured as a strain-relief, such as a strain relief to be located proximate an end or bend portion of graft device 100.

Image data 410 can include information related to the compliance of one or more portions of conduit 120, such as when algorithm 250 may identify a discrete feature 121 comprising tissue whose softness and/or flexibility may be above a threshold. In some cases, a customized portion 111 can comprise material, compliance, thickness, permeability, porosity and/or anisotropy that is different than other portions of covering 110. Algorithm 250 can analyze image data 410 and identify one or more shape changes of conduit 120 that occur over time (e.g a pre-harvested, in-situ conduit 120 that may change shape due to change in blood pressure, respiration and/or patient movement). In some cases, customized portion 111 can comprise an expandable geometry, a "loose-fitting" geometry and/or a compliance matching that of conduit 120. Algorithm 250 can analyze image data 410 and identify a customized portion 111 of covering 110 that has a modified (e.g. increased and/or decreased) porosity. For example, covering 110 may have a customized portion 111 of modified porosity proximate a discrete feature 121 of conduit 120, such as a discrete feature 121 comprising an anastomosis site (e.g. an end portion of conduit 120), and/or a segment of high curvature. Algorithm 250 can analyze image data 410 and identify a customized portion 111 of covering 110 that may have a modified compliance (e.g. increased and/or decreased compliance in a radial and/or axial direction). For example, covering 110 may have a portion 111 of modified compliance proximate a discrete feature 121 of conduit 120, such as a discrete feature 121 comprising an anastomosis site (e.g. an end portion of conduit 120 or a mid-portion for a side-to-side anastomosis), a ligament and/or tendon attachment site (e.g. when graft device 100 comprises an implant configured to function as ligament and/or a tendon), a site of segmented compliance (e.g. for radial reinforcement, kink resistance and/or peristaltic flow), and/or any combination thereof.

In some cases, algorithm 250 may be configured to create and/or modify (generally "create") a pathway of motion of a material delivery portion of MDD 300 (e.g. nozzle 310). For example, algorithm 250 can be configured to avoid one or more "off limits" locations, such as positions to be avoided that are stored in memory 220 in some cases, algorithm 250 may be configured to create a pathway of motion that may avoid one or more portions of system 10, as described by way of example herein. Algorithm 250 can be configured to create a pathway of motion that may avoid previously-produced partial portions of covering 110 while completing the production of covering 110. As described above, in some cases, covering 110 may be produced by delivery of material 350 onto conduit 120. In some cases, algorithm 250 can be configured to create a pathway of motion that avoids contact with conduit 120. As described above, in some cases, covering 110 may be produced by delivery of material 350 onto and/or at least toward a surface or tube, such as mandrel 320 described above (e.g. with or without conduit 120 in place). In some cases, algorithm 250 can be configured to create a pathway of motion that avoids contact with mandrel 320.

As described above, in some cases, covering 110 may be produced by delivery of material 350 onto conduit 120. In some cases, algorithm 250 can be configured to create a pathway of motion that avoids damaging (e.g. thermally damaging) conduit 120 (e.g. when the delivery of material 350 is at an elevated temperature), such as by minimizing heat dissipation to conduit 120 during delivery of material 350. For example, algorithm 250 can be configured to create a pathway of motion that avoids multiple passes of delivery of material 350 onto conduit 120 in neighboring regions within a time period (i.e. to allow cooling or otherwise avoid undesired accumulation of thermal energy in any one small portion of conduit 120).

In some cases, algorithm 250 may be configured to perform a self-diagnostic. Algorithm 250 can be configured to perform a self-diagnostic, such as a self-diagnostic based on signals from one or more sensors of system 10, such as a sensor 209 of processing unit 200, a sensor 309 of material delivery device (MDD) 300 and/or a sensor 409 of imaging device 400.

Sensors 209, 309 and/or 409 may individually or any combination thereof comprise one or more sensors selected from the group consisting of: an optical sensor; a laser; a magnetic sensor; an electrical sensor; an energy sensor; a pressure sensor; a force sensor; a strain gauge; a position sensor; a flow sensor; a sound sensor; an ultrasound sensor; a humidity sensor; and any combination thereof. For example, algorithm 250 can perform a self-diagnostic to assess a parameter of MDD 300 selected from the group consisting of: electrical connection status; rotational speed; translational speed; nozzle 310 status; material delivery status; temperature (e.g. via a thermocouple of other sensor of system 10); chamber environment condition (e.g. temperature or relative humidity as measured by a sensor of system 10), energy delivered (e.g. laser energy delivered); home position; a distance between two components of MDD 300; and any combination thereof.

Referring additionally to FIG. 1A, a side sectional view of a graft device comprising a covering including multiple customized portions is illustrated. Covering 110 may be positioned about conduit 120. In some cases, covering 110 may be produced by MDD 300 delivery of material directly on conduit 120. In some cases, covering 110 can be produced by MDD 300 separate from conduit 120 (e.g. onto mandrel 320 or other surface), and subsequently positioned about conduit 120. In some cases, covering 110 may have an internal profile that conformally surrounds conduit 120, such as is shown in FIG. 1A except in the area of the customized portion, tapered portion 111 c. In some cases, there may be space between one or more portions of covering 110 and conduit 120, such as one or more spaces positioned proximate one or more ends of conduit 120 (e.g to allow expansion of an end portion or other portion of conduit 120 prior to contacting covering 110), such as is shown at tapered portion 111 c.

In some cases, covering 110 may comprise fibers that are oriented to provide constraint against radial expansion that may be greater than the constraint against axial expansion, such as by aligning fibers of covering 110 more in the radial direction than in the axial direction.

Referring additionally to FIG. 1B, a side sectional view of a graft device comprising a covering including a large proportion of isotropically oriented fibers is illustrated. Covering 110 is shown positioned about conduit 120, such as when material 350 is delivered directly onto conduit 120 and/or when covering 110 may be produced and subsequently placed about conduit 120. Covering 110 of FIG. 1B may include at least a portion comprising a matrix of fibers whose orientation may be primarily isotropic, such that expansion in all directions may be relatively uniform.

Referring additionally to FIG. 1C, a side sectional view of a graft device comprising a covering including a larger proportion of circumferentially oriented fibers is illustrated. Covering 110 is shown positioned about conduit 120, such as when material 350 may be delivered directly onto conduit 120 and/or when covering 110 may be produced and subsequently placed about conduit 120. Covering 110 of FIG. 1C may include at least a portion comprising a matrix of fibers whose orientation is primarily in a relatively circumferential direction, such that expansion of covering 110 (and graft device 100) may be more limited in a radial direction than in an axial direction.

Figure 2:
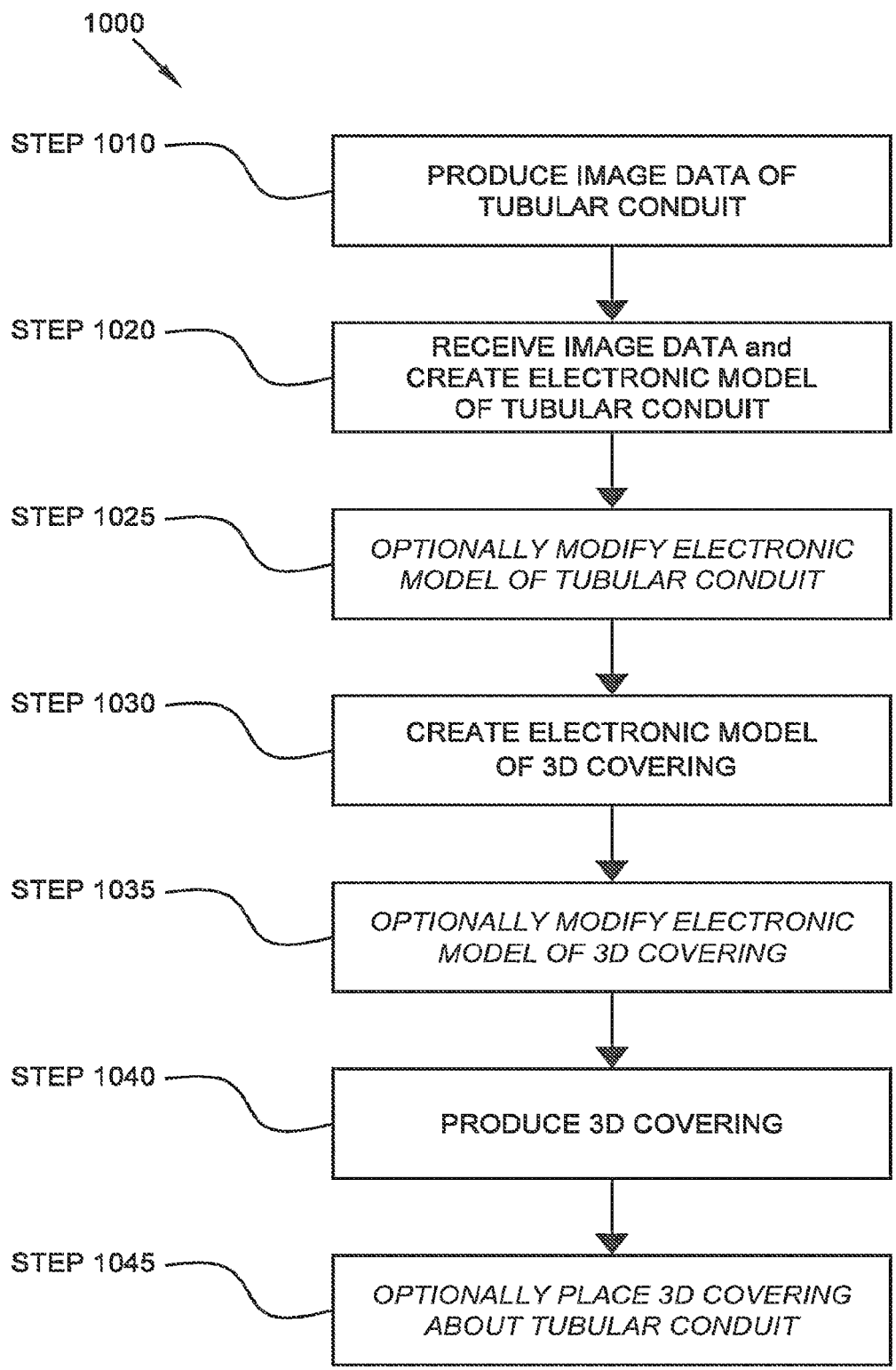
FIG. 2 illustrates a flow chart of a method of producing a graft device using the system of FIG. 1.

Referring now to FIG. 2, a flow chart of a method for producing a graft device is illustrated. Method 1000 may comprise a series of steps of producing a graft device using system 10 described herein in reference to FIG. 1. In STEP 1010, an image of a conduit 120 (e.g. a blood vessel or other tubular conduit) may be made, such as via imaging device 400 to produce image data 410. In STEP 1020, processing unit 200 may receive the image data 410, such as to create a 3D electronic model (e.g. a CAD or other electronic model) of conduit 120. In some cases, an STEP 1025 may be performed, in which the 3D electronic model of conduit 120 may be modified, such as automatically by algorithm 250 and/or manually by a user of system 10 via user interface (UI) 240.

In STEP 1030, an electronic model of a proposed covering 110 may be created by processing unit 200. In some cases, algorithm 250 may create the electronic model of the proposed covering 110 based on information selected from the group consisting of: identified discrete features 121 of conduit 120; information stored in memory 220; information input by a user via UI 240; and any combination thereof. In some cases, an STEP 1035 may be performed, in which the electronic model of the proposed covering 110 may be adjusted, such as an adjustment performed by a user of system 10 via UI 240.

In STEP 1040, covering 110 may be produced by material delivery device (MDD) 300. In some cases, covering 110 may be produced by delivery of material 350 directly onto conduit 120 in some cases, covering 110 may be produced separate from conduit 120 (e.g. on a surface, tube or other mandrel 320), and subsequently positioned about conduit 120 (e.g. in the STEP 1045) In some cases, a mandrel 320 may be produced by MDD 300 as described herein.

Figure 3:
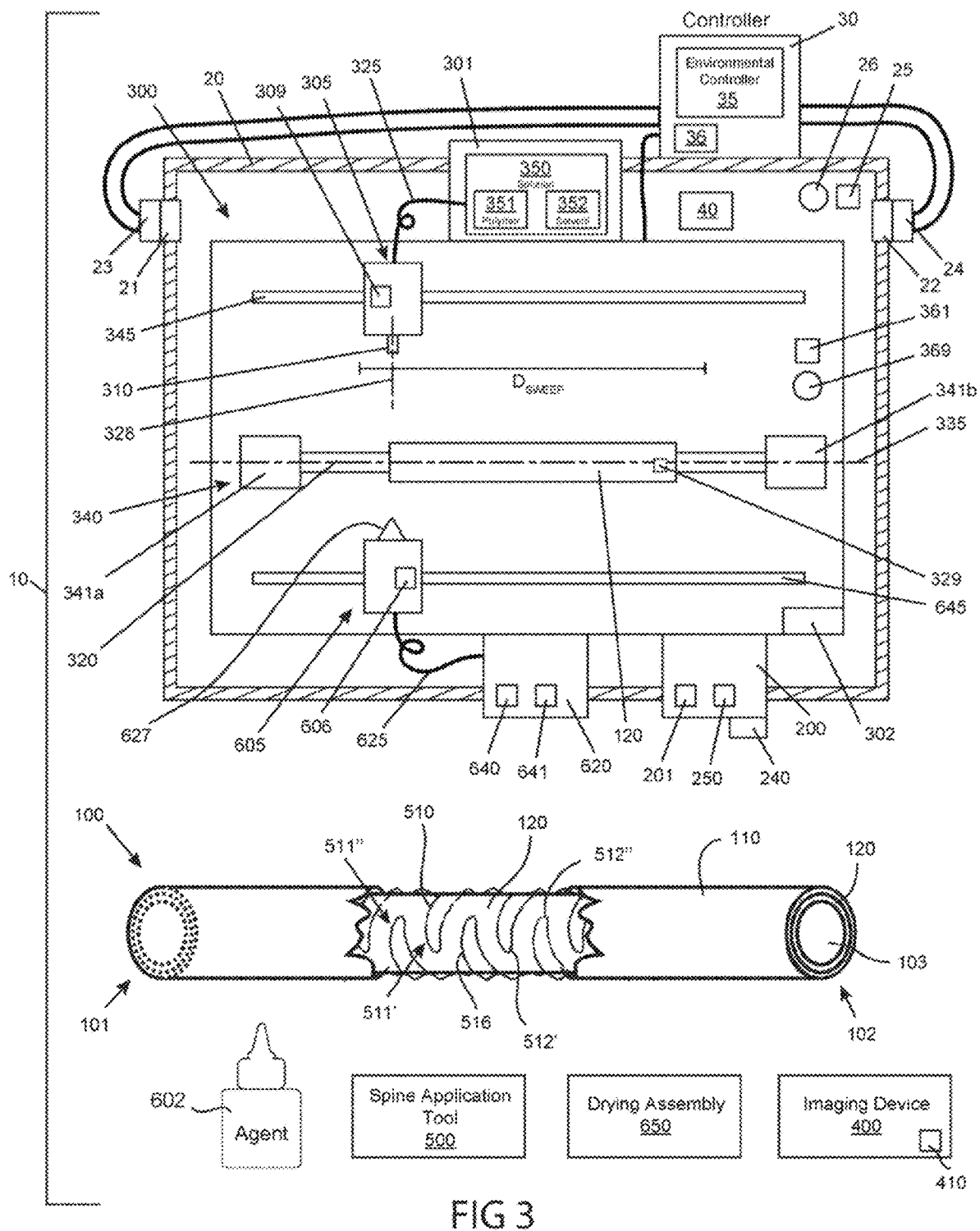
FIG. 3 illustrates a schematic view of a particular embodiment of the system of FIG. 1.

Referring now to FIG. 3, a schematic view of a system for producing an implantable device is illustrated. System 10 may include various components and assemblies (hereinafter "components") used to produce an implantable device, such as graft device 100 shown. System 10 may comprise processing unit 200, material delivery device (MDD) 300 and imager 400, and one or more of these can be of similar construction and arrangement and/or include similar components to those described herein in reference to FIG. 1. Imager 400 may comprise an imaging device and may produce image data 410. Image data 410 can represent geometric and other information related to conduit 120 (e.g. a blood vessel, other tubular conduit and/or other patient tissue) and/or any portion of a patient's anatomy. Processing unit 200 can include algorithm 250, which can be used to produce a construction signal 201 based on the image data 410. MDD 300 can comprise a material delivery device used to produce an implantable device that is based on construction signal 201. For example, MDD 300 can deliver one or more materials, material 350, to produce an implantable device, and the pattern of the delivery of the material 350 can be based on construction signal 201 (and correspondingly based on image data 410). In some cases, MDD 300 may produce a covering 110 which may be positioned about conduit 120 to produce graft device 100. Covering 110 can be positioned about conduit 120 after covering 110 may be produced by MDD 300, or MDD 300 can deliver material 350 directly onto conduit 120 while producing covering 110.

Graft device 100 can be constructed and arranged to perform or otherwise function as a bypass graft, such as a coronary artery bypass graft or a peripheral artery bypass graft. In some cases, graft device 100 is constructed and arranged as a neo-vessel, such as a neo-artery and/or a neo-vein conduit 120 can include living tissue and/or artificial materials. In some cases, conduit 120 may comprise living tissue (e.g. harvested tissue), such as a segment or other portion of tissue selected from the group consisting of: saphenous vein; vein; artery, urethra; intestine; esophagus; ureter; trachea; bronchi; duct; fallopian tube; and any combination thereof or other tissues. In some cases, conduit 120 can comprise an artificial material selected from the group consisting of: polytetrafluoroethylene (PTFE); expanded PTFE (ePTFE); polyester; polyvinylidene fluoride/hexafluoropropylene (PVDF-HFP); silicone; polyethylene; polypropylene; polyester-based polymer; polyether-based polymer; thermoplastic rubber; and any combination thereof or other materials. Graft device 100 may comprise first end 101, second end 102, and a lumen 103 extending from first end 101 to second end 102. System 10 may include a material delivery device, MDD 300, may be configured to deliver material 350 to produce covering 110. Material 350 can comprise a biocompatible material such as a biocompatible metal and/or plastic. Material 350 can comprise a first material 351 (e.g a polymer) and a second material 352 (e.g. a solvent). Material delivery device (MDD) 300 can comprise a 3D printing device. In some cases, MDD 300 may comprise a device selected from the group consisting of: a 3D printer; a layer printing device; an electrospinning device; a melt-spinning device, a melt-electrospinning device, a misting assembly, a sprayer; an electrosprayer; a fused deposition device; a selective laser sintering device; a fiber dispenser; a wire dispenser; a thread dispenser; a resin deposition device, such as a UV-curable resin deposition device; a stereolithography device; a phase separation device; a wet spinning device; a dip coating device, a lathe; a milling machine; a chemical etching device, a plasma etching device; a negative mold-over device; an injection molding device; and any combination thereof. In some cases, MDD 300 may comprise a second material delivery device, such as a material delivery device selected from the group consisting of: an electrospinning device; a melt-spinning device; a melt-electrospinning device; a misting assembly; a sprayer; an electrosprayer; a fuse deposition device; a selective laser sintering device; a three-dimensional printer; and any combination thereof. In some cases, second material 352 or another portion of material 350 may comprise a solvent or other material that may be desired to be removed before covering 110 may be implanted in the patient. In some cases, system 10 can be configured to remove second material 352 (e.g. a solvent), accelerate the removal of second material 352 and/or at least reduce the amount of second material 352 present in conduit 120, covering 110, graft device 100, chamber 20 and/or another component of system 10 (hereinafter "remove second material 352" or "remove solvent") in some cases, system 10 can be configured to reduce injury to the conduit 120 by one or more solvents (e.g. reduce injury to living tissue such as living vein tissue). System 10 can include one or more sensors, such as sensors 26, 36, 329, 309, 369 and/or 606 shown and described in detail herein. Sensors 26, 36, 329, 309, 369 and/or 606 can provide a signal related to the creation of covering 110 (e.g. related to the presence of one or more solvents and/or a signal otherwise used to perform a solvent-reducing process and/or to reduce injury to a conduit 120 by one or more solvents).

System 10 can include a mandrel 320 and a material delivery device (MDD) 300 can comprise a rotating assembly 340 configured to rotate mandrel 320. In the embodiment shown in FIG. 3, mandrel 320 may be slidingly inserted into conduit 120, and subsequently engaged with rotating assembly 340. In some cases, covering 110 may be produced on mandrel 320 (e.g. material 350 is delivered onto mandrel 320), as described herein in reference to FIG. 1 in some cases, covering 110 may be produced without the use of mandrel 320. MDD 300 can include material dispenser 301 configured to dispense one or more materials, such as material 350 shown. Material 350 can comprise one or more materials as described herein in reference to FIG. 1. Material 350 can include a mixture of one or more first materials 351 (e.g. one or more polymers), one or more second materials 352 (e.g. one or more solvents) and/or other materials used to produce covering 110. Material 350 can comprise a cartridge or other reservoir surrounding first material 351 and/or second material 352, the reservoir being fluidly attachable to material dispenser 301 by an operator of system 10.

System 10 can include an environmentally controllable chamber, chamber 20 shown, which surrounds at least a portion of mandrel 320 (e.g. surrounding at least conduit 120 and covering 110 during the creation of graft device 100). Chamber 20 can surround one or more portions of material delivery assembly 305 and/or modification assembly 605 described herein. In some cases, chamber 20 may comprise a disposable cartridge and/or at least a portion of chamber 20 is disposable (e.g. used to create implants for a single patient). Chamber 20 can be configured to remove solvents or other potentially harmful materials (collectively "remove solvent" herein) during and/or after production of covering 110.

System 10 may include controller 30 which is configured to provide control signals and/or receive information signals. Controller 30 can be configured to control one or more of: material delivery assembly 305 (e.g. to control the flow rate of material 350 into material delivery assembly 305); rotating assembly 340 (e.g to control the rotation of mandrel 320), linear drive assembly 345 (e.g. to control the translation rate or position of material delivery assembly 305); modification assembly 605 (e.g. to control delivery of material by modification assembly 605, delivery of energy by modification assembly 605 and/or removal of a portion of covering 110 by modification assembly 605); linear drive assembly 645 (e.g. to control the translation rate or position of modification assembly 605); voltage applied to mandrel 320 (e.g. voltage provided by power supply 302); and any combination thereof. Controller 30 can comprise environmental controller 35. Environmental controller 35 can be configured to remove solvents. In some cases, environmental controller 35 can be configured to control an environmental parameter within chamber 20, such as an environmental parameter selected from the group consisting of: temperature; humidity; pressure; solvent concentration; and any combination thereof. Environmental controller 35 or another component of controller 30 can comprise one or more fans or other gas propulsion mechanisms, such as to provide air or other gas to inlet port assembly 21 (e.g. via the tube shown positioned between controller 30 and inlet port assembly 21) or extract gas from chamber 20 via outlet port assembly 22 (e.g. via the tube shown positioned between controller 30 and outlet port assembly 22) In some cases, controller 30 may comprise an alarm assembly, which can be constructed and arranged to be activated when an undesired state may be detected (e.g. an undesired concentration or amount of solvent present, or other undesired state related to a solvent), such as to notify an operator of system 10. Controller 30 can comprise an alarm assembly constructed and arranged to provide an alert selected from the group consisting of: audible alert; visual alert; tactile alert; and any combination thereof. In some cases, when an undesired state may be detected (e.g. an unacceptable concentration of solvent within chamber 20, within conduit 120 and/or within covering 110 is detected), creation of covering 110 by system 10 may be stopped.

In some cases, system 10 may comprise one or more similar or dissimilar spines 510, and graft device 100 may comprise one or more of the spines 510. In some cases, material delivery device (MDD) 300 may be configured to produce spine 510, such as when MDD 300 may comprise at least a 3D printer. System 10 can include spine application tool 500, which can comprise a manual or automated (e.g. robotic) tool used to place spine 510 about conduit 120, such as between one or more layers of covering 110 (e.g between an inner layer with a first thickness, and an outer layer with a second thickness about twice as thick as the first layer's thickness). In some cases, system 10 can include one or more tools, components, assemblies and/or otherwise be constructed and arranged as described in applicant's copending U.S. patent application Ser. No. 15/023,265, filed Mar. 18, 2016, the content of which is incorporated herein by reference in its entirety for all purposes.

In some cases, a system for producing a graft device may comprise a tubular conduit, a first spine; and a fiber matrix delivery assembly constructed and arranged to deliver a fiber matrix to surround the tubular conduit.

In some cases, a system may comprise a second spine. The first spine can comprise a first inner diameter and the second spine can comprise a second inner diameter different than the first inner diameter. The first inner diameter and the second inner diameter can comprise approximate diameters selected from the group consisting of: about 4.0 mm; about 4.7 mm and about 5.5 mm. The system can comprise a third spine. The first spine can comprise a first inner diameter, the second spine can comprise a second inner diameter different than the first inner diameter, and the third spine can comprise a third inner diameter different than the first inner diameter and the second inner diameter. The first inner diameter can comprise a diameter of about 4.0 mm, the second inner diameter can comprise a diameter of about 4.7 mm and the third inner diameter can comprise a diameter of about 5.5 mm.

In some cases, the system may comprise a spine application tool constructed and arranged to apply a spine about the tubular conduit. The spine application tool can be constructed and arranged to laterally apply the spine about the tubular conduit. The fiber matrix can comprise an inner layer and an outer layer, and the spine application tool can be constructed and arranged to apply the spine between the inner and outer layer of the fiber matrix. The spine application tool can comprise an automated tool. The spine application tool can comprise a robotic tool. The fiber matrix delivery assembly can comprise the spine application tool. The spine application tool can comprise a scissor-like construction.

In some cases, the system may comprise a trimming tool constructed and arranged to trim one or both ends of the spine. The trimming tool can be constructed and arranged to trim the fiber matrix. The trimming tool can comprise a tool selected from the group consisting of: scissors; scalpel, laser cutter; radiofrequency cutter; and any combination thereof. The fiber matrix delivery assembly can comprise the trimming tool. The trimming tool may comprise an automated tool. The trimming tool may comprise a robotic tool. The fiber matrix delivery assembly can comprise the trimming tool. The trimming tool can comprise a laser. In some cases, the system may comprise a surface modifying agent.

In some cases, the system may comprise a spine fabrication tool constructed and arranged to produce the spine. The spine fabrication tool can comprise a rod and a plurality of pins. The rod can comprise a relatively linear rod. The rod can comprise at least a non-linear portion. The fiber matrix delivery assembly can comprise the spine fabrication tool. The fiber matrix delivery assembly can comprise an electrospinning device constructed and arranged to produce the spine. The fiber matrix delivery assembly can comprise a three-dimensional printer constructed and arranged to produce the spine. The fiber matrix delivery assembly can comprise a stereolithography device constructed and arranged to produce the spine. The fiber matrix delivery assembly may comprise a fuse deposition device constructed and arranged to produce the spine.

Also provided herein may be systems and methods for producing a graft device commising a conduit, a surrounding fiber matrix and a spine. Systems may include an electrospinning device and/or other fiber or fiber matrix delivering assembly. In some cases, the spine may comprise a component that may be applied, placed and/or inserted, such as by the fiber matrix delivery assembly (e.g. automatically or semi-automatically) or with a placement or insertion tool (e.g. manually).

System can include a tool for applying spine about conduit, such as spine application tool constructed and arranged to engage an inner and/or outer portion of spine and subsequently cause spine to radially expand to be placed (e.g. laterally placed) about conduit. In some cases, tool can be constructed and arranged to maintain the geometry (e.g. shape or alignment) of one or more spines, such as to maintain the geometry of one or more spines during shipping and/or storage.

System can include one or more agents for modifying the surface of spine, conduit and/or a fiber matrix applied by fiber matrix delivery assembly.

System can include one or more tools for cutting or otherwise trimming one or more spines to a particular length, such as trimming tool. Spine and one or more portions of an applied fiber matrix can be trimmed prior to, during or after application of one or more polymers from polymer solution dispenser by fiber matrix delivery assembly. Trimming tool can be a manual tool and/or an at least partially automated tool, such as a tool integrated into fiber matrix delivery assembly. In some cases, a trimming tool may comprise one or more cutting tools such as a cutting tool selected from the group consisting of: scissors; scalpel; laser cutter; radiofrequency cutter; and combinations thereof.

System can include one or more fasteners configured to apply a retention force between at least two of tubular conduit, spine and an applied fiber matrix comprising one or more polymers from polymer solution dispenser. Fasteners can comprise one or more elements selected from the group consisting; of adhesive; staple; clip; suture, barb; hook, and any combination thereof. In some cases, fasteners comprise at least about 4 fasteners. In some cases, one or more fasteners may be attached to and/or attachable to spine. Fasteners can be applied to conduit and/or spine when conduit and/or spine are positioned about mandrel. Fasteners can be positioned within about 1 cm of one or both ends of conduit. In some cases, one or more fasteners may comprise a material similar to the material of spine, such as the material of an interdigitating projection of spine as described herein.

System can include spine fabrication tool which may be constructed and arranged to produce one or more spines. Spine fabrication tool can be constructed and arranged to resiliently bias spine, such as in a relatively linear or non-linear shape. In some cases, a spine fabrication tool may be integral to fiber matrix delivery assembly. In some cases, a fiber matrix delivery assembly can create the spine with an assembly selected from the group consisting of: an electrospinning device; a three-dimensional printer; a stereolithography device; a fuse deposition device, and any combination thereof. In some cases, a spine fabrication tool may be a separate device. In some cases, a spine fabrication tool may comprise one or more rods about which a filament is wrapped to create spine, such as two or more rods with different outer diameters used to produce two or more spines with different inner diameters.

A system can include one or more patterning masks, such as a physical or chemical mask used to prevent fiber matrix from covering one or more portions of conduit. In some cases, a system may include an aperture plate. Aperture plate can comprise a stencil-like pattern configured to prevent or reduce delivery of fiber to certain portions of the outer surface of conduit. In some cases, an aperture plate can comprise a stencil-like pattern that causes fiber matrix to include a pattern of relief slots. In some cases, an aperture plate can be configured to induce one or more changes to the electromagnetic (EM) field within electrospinning device. These one or more changes to the EM field can be configured to cause variations in the delivered fiber pathway, resulting in a patterned fiber matrix. In some cases, a mandrel can have modified electrical characteristics, such as modified conductivity along its length, configured to modify the EM field to cause patterned fiber deposition.

A system can include a power supply, power supply may be configured to provide the electric potentials to nozzle and mandrel, as well as to supply power to other components of system such as drive assemblies and and modification assembly. Power supply can be connected, either directly or indirectly, to at least one of mandrel and conduit. Power can be transferred from power supply to each component by, for example, one or more wires.

A system can include inlet and/or outlet ports. Ports may be configured to control the environment surrounding the environment surrounding mandrel. A port can be configured to be both an inlet port and an outlet port. A system can include a housing. A housing may be attachable to electrospinning device and defining a chamber surrounding assemblies and/or and/or mandrel, such that the ports can control a more limited (smaller) environment surrounding assemblies and/or and/or mandrel. In some cases, the ports can be used to introduce or remove one or more gases, introduce or remove humidity, control temperature, control sterility, provide other environmental controls, and any combination thereof.

Mandrel 320 can comprise a metal mandrel, such as a mandrel constructed of 304 or 316 series stainless steel. Mandrel 320 can comprise a mirror-like surface finish, such as a surface finish with an $R_a$ of about 0.1 micrometers (μm) to about 0.8 μm. Mandrel 320 can comprise a length of up to about 45 centimeters (cm), such as a length of from about 30 cm to about 45 cm, or from about 38 cm to about 40 cm. In some cases, system 10 may include multiple mandrels 320 with multiple geometries, such as a set of mandrels 320 with different diameters (e.g. diameters of about 3.0 millimeter (mm), about 3.5 mm, about 4.0 mm, and/or about 4.5 mm). In some cases, MDD 300 may be configured to automatically detect the mandrel 320 diameter (e.g. and to adjust rotation rate and/or another system parameter based on the detected mandrel 320 diameter). One or both ends of mandrel 320 may be inserted into driving elements of rotating assembly 340, motors 341 *a* and 341 *b*, respectively, such that mandrel 320 can be rotated about axis 335 during creation of covering 110. In some cases, a single motor may drive one end of mandrel 320, with the opposite end attached to a rotatable attachment element (e.g a bearing) of MDD 300.

Mandrel 320 can comprise a porous mandrel, such as a mandrel configured to deliver one or more drugs or other agents to covering 110 and/or conduit 120 prior to, during and/or after creation of covering 110. In some cases, an agent 602 may be delivered to (e.g. coated onto) covering 110 and/or conduit 120 via a porous mandrel 320, via material delivery assembly 305 (e.g. via nozzle 310), via modification assembly 605 (e.g. via modifying element 627), or otherwise. Agent 602 can comprise a solvent-reducing material (e.g. a material configured to absorb solvent and a material configured as a barrier that prevents solvent from reaching covering 110 and/or conduit 120), a solvent neutralizing material, a hydrating solution and/or a preservative solution. In some cases, agent 602 may comprise a preservative solution comprising one or more materials selected from the group consisting of: chilled fluid, fluid chilled to about 4° C.; water; saline; heparin, heparinized saline, blood; ringers solution; and any combination thereof. In some cases, agent 602 may comprise a material configured as both a barrier and a solvent-absorbing material.

MDD 300 can include one or more material delivery assemblies, and in the illustrated embodiment, MDD 300 may include material delivery assembly 305.

Material delivery assembly 305 may comprise nozzle 310. Nozzle 310 may include an orifice constructed and arranged to deliver material 350 to produce covering 110. Nozzle 310 can be a tubular structure including nozzle central axis 328. Nozzle 310 can be constructed of stainless steel, such as passivated 304 stainless steel. In some cases, nozzle 310 may comprise an outer tube and an inner tube, such as to avoid icicle formation about nozzle 310. For example, material delivery assembly 305 and/or nozzle 310 can be constructed and arranged as described in applicant's co-pending application U.S. patent application Ser. No. 15/036,304, filed May 12, 2016.

Electrospinning device can include one or more nozzle assemblies. In some cases, an electrospinning device may include nozzle assembly, which may include one or more nozzles. Nozzle assembly may be fluidly attached to polymer solution dispenser via delivery tube. Dispenser may comprise a solution of one or more polymers, solvents and/or other materials. Nozzle assembly may be operably attached to a linear drive assembly configured to translate nozzle assembly in at least one direction.

In some cases, a modifying element may comprise a nozzle, such as a nozzle configured to deliver a fiber modifying agent and/or a graft modifying agent. A reference to a "nozzle" and "nozzle assembly" in singular or plural form can include one or more nozzles, such as nozzle, and one or more assemblies, such as nozzle assemblies.

Nozzle can be constructed of stainless steel. In some cases, nozzle may have a tubular construction with a length of about 1.5 inches, an inner diameter (ID) of about 0.047 inches and an outer diameter (OD) of about 0.065 inches Nozzle can include an insulating coating, with the tip of nozzle exposed (e.g. non-insulated), such as with an exposed length of about 1 centimeter (cm). Nozzle geometry and electrical potential voltages applied between nozzle and mandrel may be chosen to control fiber generation. In some cases, fibers may be produced with an average diameter from about 1.0 micrometer (µm) to about 20 µm, such as from about 5 µm to about 15 µm, or from about 6 µm to about 12 µm.

A mandrel may be positioned in a particular spaced relationship from nozzle assembly and/or modification assembly, and nozzle and/or modifying element, respectively. In some cases, a mandrel may be positioned above and below assemblies and, respectively. In some cases, a mandrel can be positioned either above, below, to the right and/or or to the left of, assembly and/or assembly. The distance between mandrel and the tip of nozzle and/or modifying element can be less than about 20 cm, or less than about 15 cm. In some cases, the tip of nozzle and/or modifying element may be about 12.5 cm from mandrel. In some cases, multiple nozzles and/or multiple modifying elements, for example components of similar or dissimilar configurations, can be positioned in various orientations relative to mandrel. In some cases, the distance between nozzles and/or modifying elements and mandrel may vary along the length of mandrel, such as to create a varying pattern of fiber matrix along conduit. In some cases, a nozzle and/or modifying element distances from mandrel can vary continuously during the electrospinning process and/or the distance can vary for one or more set periods of time during the process.

In some cases, an electrical potential may be applied between nozzle and one or both of conduit and mandrel. The electrical potential can draw at least one fiber from nozzle assembly to conduit. Conduit can act as the substrate for the electrospinning process, collecting the fibers that may be drawn from nozzle assembly by the electrical potential. In some cases, a mandrel and/or conduit may have a lower voltage than a nozzle to create the desired electrical potential.

In some cases, a polymer solution, stored in polymer solution dispenser, may be delivered to nozzle assembly through polymer solution delivery tube. The electrical potential between nozzle and conduit and/or mandrel can draw the polymer solution through nozzle of nozzle assembly. Electrostatic repulsion that may be caused by the fluid becoming charged from the electrical potential, may counteract the surface tension of a stream of the polymer solution at nozzle of the nozzle assembly. After the stream of polymer solution may be stretched to its critical point, one or more streams of polymer solution may emerge from nozzle of nozzle assembly, and/or at a location below nozzle assembly, and may move toward the negatively charged conduit. Using a volatile solvent, the solution may dry substantially during transit and the fiber may be deposited on conduit.

Material delivery assembly 305 may be fluidly attached to material dispenser 301 via delivery tube 325. Material delivery assembly 305 may receive material 350 and may deliver material 350 to produce covering 110 (e.g. delivers material 350 to mandrel 320 and/or conduit 120). Material delivery assembly 305 can comprise one or more pumping mechanisms, such as a syringe pump (e.g. a syringe pump in which material 350 is contained within the syringe), a peristaltic pump, a displacement pump and/or other pumping mechanism. Material delivery assembly 305 can comprise linear drive assembly 345. Linear drive assembly 345 may translate nozzle 310 in at least one direction for a linear travel distance $D_{SWEEP}$ as shown. In some cases, linear drive assembly 345 may reciprocally translate nozzle 310 along the distance $D_{SWEEP}$ In some cases, $D_{SWEEP}$ may comprise a length of about 30 centimeters (cm), such as a length of at least about 10 cm, about 20 cm, about 30 cm, about 35 cm, or about 40 cm. In some cases, linear drive assembly 345 may move nozzle 310 based on a construction signal 201 produced by processing unit 200, such as a construction signal 201 based on image data of conduit 120 produced by imaging device 400.

As described herein, mandrel 320 can be rotated about axis 335 during the delivery of material 350 by material delivery assembly 305 to produce covering 110 in some cases, material delivery assembly 305 (e.g. and nozzle 310) can rotate about mandrel 320 during delivery of material 350 (e.g. as material delivery assembly 305 and mandrel 320 may translate relative to each other via translational motion of either or both).

In some cases, material 350 may comprise two or more polymers, such as a first polymer with a first hardness, and a second polymer with a second hardness different than the first hardness. Material 350 can comprise a mixture of similar or dissimilar amounts of polyhexamethylene oxide soft segments, and aromatic methylene diphenyl isocyanate hard segments. Material 350 can comprise one or more solvents, such as hexafluoro-2-propanol (HFIP) (e.g. HFIP with an about 99.97% minimum purity). Material 350 can comprise one or more polymers in a concentrated solution fully or at least partially solubilized within a solvent and comprise a polymer weight to solvent volume ratio from about 20% to about 35%, where a concentration may be from about 24% to about 26% (more specifically from about 24.5% to about 25.5%). Material 350 can comprise one or more materials with a molecular weight average (Mw) from about 80,000 to about 150,000 (polydispersity index (PDI)—molecular weight per molecular number (Mw/Mn) from about 2.1 to about 3.5). Material 350 can comprise a solution with a viscosity from about 2000 centipoise (cP) to about 2400 cP (measured at about 25° C. and with shear rate equal to about 20 s⁻) Material 350 can comprise a solution with a conductivity from about 0.4 microSiemens per centimeter (ρS/cm) to about 1.7 ρS/cm (measured at a temperature from about 20° C. to about 22° C.) Material 350 can comprise a solution with a surface tension from about 21.5 milliNewtons per meter (mN/m) to about 23.0 mN/m (measured at about 25° C.).

In some cases, system 10 may be constructed and arranged to produce a covering 110 with a thickness (absent of any spine 510) of from about 220 µm to about 280 µm. Covering 110 can comprise a matrix of fibers with a diameter from about 6 µm to about 15 µm, such as a matrix of fibers with an average diameter of from about 7.8 µm to about 8.6 µm. Covering 110 can comprise a porosity of from about 0% to about 99%, such as from about 30% to about 80%, from about 40% to about 80%, or from about 50% to about 70% In some cases, covering 110 may comprise an average compliance ("compliance" herein) from about 0.2× $10^{-4}$/millimeter of mercury (mmHg) to about $3.0 \times 10^{-4}$/mmHg when measured in arterial pressure ranges. In some cases, covering 110 may comprise an elastic modulus from about 10 MPa to about 18 MPa.

Material delivery assembly 305 can be configured to deliver material 350 to nozzle 310 at a flow rate of from about 10 milliliters per hour (mi/br) to about 25 ml/hr, such as at a flow rate of from about 15 ml/hr to about 20 ml/hr, such as about 15 ml/hr or about 20 ml/hr.

As described above, in some cases, system 10 may be constructed and arranged to produce a graft device 100 including a spine 510. Spine 510 can comprise multiple spines 510 with different inner diameters (IDs), such as multiple spines with IDs of about 4.0 millimeters (mm), about 4.7 mm, and/or about 5.5 mm. Spine 510 can comprise a filament 516 with a diameter of about 0.4 mm (e.g. for a spine with an ID from about 4.0 mm to about 4.7 mm). Spine 510 can comprise a filament 516 with a diameter of about 0.5 mm (e.g for a spine with an ID from about 4.8 mm to about 5.5 mm) Spine 510 can comprise a series of interdigitating fingers spaced about 0.125 inches from each other so that the recurring unit of spine including one left finger and one right finger occurs about every 0.25 inches. This recurring feature length can have a range comprised from about 0.125 inches to about 0.375 inches. The fingers can overlap in a symmetric or asymmetric pattern, such as an overlap of opposing fingers from about 2.5 mm to about 1.0 mm around the circumferential perimeter of spine 510. Spine 510 can be heat treated to achieve a resilient bias. Spine 510 can be surface-treated (e.g. with dimethylformamide) to increase the surface roughness and reduce crystallinity (e.g. to improve solvent-based adhesion with the covering 110).

Spine 510 can include one or more portions that may be resiliently biased, such as a resilient bias may be configured to provide a radial outward force at locations proximate ends 101 and/or 102, such as to provide a radial outward force to support or enhance the creation of an anastomosis during a cardiovascular bypass procedure. In some cases, spine 510 may include one or more portions that are malleable.

Spine 510 can include multiple curved projections 511' and 511", collectively 511. One or more projections 511' (such as each projection) may include a tip portion 512' and one or more projections 511" (such as each projection) may include a tip portion 512" (collectively, tip portions 512). Tip portions 512 can be arranged in the overlapping arrangement shown in FIG. 3. Projections 511' and 511" can comprise a first and second support portion, respectively, that are arranged such that at least one rotates relative to the other to create an opening to receive conduit 120. In some cases, one or more tip portions 512 (such as each tip portion) can comprise a diameter from about 0.020 inches to about 0.064 inches, such as a diameter about 0.042 inches one or more projections 511 (such as each projection) can comprise a loop of a filament (e.g a loop of a continuous filament), and projections 511' and 511" can be arranged in an interdigitating arrangement such as the alternating, interdigitating arrangement shown in FIG. 3 in some cases, the interdigitating projections 511' and 511" can overlap (e.g spine 510 covers more than 360° of conduit 120). In some cases, projections 511' and 511" may be arranged with an overlap of at least about 1.0 millimeters (mm), at least about 1.1 mm or at least about 1.4 mm. In some cases, spine 510 can be constructed and arranged as described in applicant's copending U.S. patent application Ser. No. 15/023,265, filed Mar. 18, 2016, the content of which is incorporated herein by reference in its entirety for all purposes.

A graft device can include a spine, such as to prevent luminal narrowing, radial collapse, kinking and/or other undesired movement of the graft device (e.g. movement into an undesired geometric configuration), such as while implanting the graft device during a surgical procedure and/or at a time after implantation. The spine can be placed inside the tubular conduit, between the tubular conduit and the fiber matrix, between layers or within layers of the fiber matrix and/or outside the fiber matrix. The spine can comprise a biodegradable or bioerodible (hereinafter "biodegradable") material or otherwise be configured to provide a temporary support to the graft device. In some cases, a spine can comprise one or more portions including durable or otherwise non-biodegradable materials configured to remain intact for long periods of time when implanted, such as at least about 6 months or at least about 1 year.

Also provided herein are systems and methods for producing a graft device comprising a conduit, a surrounding fiber matrix and a spine. Systems may include an electrospinning device and/or other fiber or fiber matrix delivering assembly. In some cases, the spine may comprise a component that may be applied, placed and/or inserted, such as by the fiber matrix delivery assembly (e.g. automatically or semi-automatically) or with a placement or insertion tool (e.g. manually).

Graft device can include spine. Spine may be constructed and arranged to prevent graft device from undergoing undesired motion such as kinking or other narrowing, such as during implantation procedure and/or while under stresses endured during its functional lifespan. In some cases, spine may surround conduit, positioned between conduit and fiber matrix, where spine may comprise a diameter approximating the outer diameter of conduit. In some cases, spine, in whole or in part, can be between one or more layers of fiber matrix. In some cases, spine, in whole or in part, can surround fiber matrix. In some cases, spine may be positioned within conduit. In some cases, multiple spines can be included, each surrounding tubular conduit, surrounding fiber matrix and/or positioned between two or more layers of fiber matrix.

Spine can be constructed and arranged to provide one or more functions selected from the group consisting of minimizing undesirable conditions, such as buckling, conduit deformation, luminal deformation, stasis, flows characterized by significant secondary components of velocity vectors such as vortical, recirculating or turbulent flows, luminal collapse, and/or thrombus formation; preserving laminar flow such as preserving laminar flow with minimal secondary components of velocity, such as blood flow through graft device, blood flow proximal to graft device and/or blood flow distal to graft device; preventing bending and/or allowing proper bending of the graft device, such as bending that occurs during and/or after the implantation procedure; preventing accumulation of debris; preventing stress concentration on the tubular wall; maintaining a defined geometry in tubular conduit; preventing axial rotation about the length of tubular conduit, and combinations thereof. Spine and fiber matrix can comprise similar elastic moduli, such as to avoid dislocations and/or separations between the two components over time, such as when graft device undergoes cyclic motion and/or strain.

Spine can be applied around conduit prior to, during and/or after application of fiber matrix to graft device. For example, spine can be applied prior to application of fiber matrix when spine may be positioned between conduit and fiber matrix. Spine can be applied during application of fiber matrix when spine may be positioned between one or more layers of fiber matrix. Spine can be applied after application of fiber matrix when spine may be positioned outside of fiber matrix. Spine can be applied about conduit and/or at least a layer of fiber matrix with one or more tools.

Spine can include one or more portions that are resiliently biased, such as a resilient bias configured to provide a radial outward force at locations proximate ends and/or, such as to provide a radial outward force to support or enhance the creation of an anastomosis as described herein spine can include one or more portions that are malleable.

In some cases, a spine may include multiple curved projections and, singly or collectively projections. One or more projections, such as each projection may include a tip portion (singly or collectively, tip portions). In some cases, one or more tip portions or each tip portion can comprise a diameter from about 0.020 inches to about 0.064 inches, such as a diameter of about 0.042 inches. One or more projections or each projection can comprise a loop of a filament (e.g. a loop of a continuous filament), and projections and can be arranged in an interdigitating arrangement such as the alternating, interdigitating arrangement. In some cases, the interdigitating projections and can overlap (e.g. spine covers more than 360° of conduit). In some cases, projections can be arranged with an overlap of at least about 1.0 mm, at least about 1.1 mm or at least about 1.4 mm. A set of projections can comprise first support portion, whose tip portions can be collectively deflected or otherwise rotated towards the top of the page A set of projections can comprise a second support portion, whose tip portions can be collectively deflected or otherwise rotated towards the bottom of the page. The rotations of first support portion and second support portion may create an opening that may allow a spine to approach and surround conduit from the side (e.g. laterally engage conduit and/or at least a layer of fiber matrix already applied to conduit). Rotation of first support portion relative to second support portion and/or rotation of second support portion relative to first support portion can be performed with one or more spine application tools.

A spine can comprise at least three projections, such as at least six projections. In sonic cases, a spine may include at least two projections for every about 15 mm of length of spine, such as at least two projections for every about 7.5 mm of length of spine, or at least two projections for every about 2 mm of length of spine. In some cases, spine comprises two projections for each about 6.5 mm of length of spine.

A spine can comprise one or more continuous filaments, such as three or less continuous filaments, two or less continuous filaments, or a single continuous filament. In some cases, spine may comprise a continuous filament of at least about 15 inches long, or at least about 30 inches long such as when spine comprises a length of about 3.5 inches. In some cases, filament may comprise a length (e.g. a continuous length or a sum of segments with a cumulative length) of about 65 inches (e.g. to create a 4.0 mm diameter spine), or a length of about 75 inches (e.g. to create a 4.7 mm diameter spine), or a length of about 85 inches (e.g. to create a 5.5 mm diameter and/or 3.5 inches long spine). A filament can comprise a relatively continuous cross section, such as an extruded or molded filament with a relatively continuous cross section. Spine can comprise a filament including at least a portion with a cross section with a geometry selected from the group consisting of: elliptical; circular; oval; square; rectangular; trapezoidal; parallelogram-shaped; rhomboid-shaped; T-shaped, star-shaped, spiral-shaped; (e.g. a filament comprising a rolled sheet); and any combination thereof. A filament can comprise a cross section with a major axis from about 0.2 mm to about 1.5 mm in length, such as a circle or oval with a major axis less than or equal to about 1.5 mm, less than or equal to about 0.8 mm, or less than or equal to about 0.6 mm, or from about 0.4 mm to about 0.5 mm. Filament can comprise a cross section with a major axis greater than or equal to about 0.1 mm, such as a major axis greater than or equal to about 0.3 mm. In sonic cases, the major axis and/or cross sectional area of filament may be proportionally based to the diameter of spine (e.g. a larger spine diameter correlates to a larger filament diameter, such as when a range of different diameter spine are provided in a kit.

A spine can comprise a tubular structure, such as a full circumferential (e.g at least) 360° or partial circumferential tubular structure. In some cases, a spine may comprise an inner diameter $D_S$ that may approximate the outer diameter of tubular conduit, diameter $D_{TS}$. In some cases, spine may comprise an inner diameter $D_S$ that may approximate the outer diameter of a partial layer of fiber matrix covering tubular conduit. In some cases, a spine may comprise an inner diameter $D_S$ that may approximate the outer diameter of a full layer of fiber matrix covering tubular conduit. A spine can comprise an inner diameter of at least about 2 mm or an inner diameter of no more than about 20 mm. A spine can comprise a length from about 2 inches to about 6 inches, such as a length from about 3 inches to about 5 inches. In some cases, a spine may comprise multiple tubular structures with lengths from about 1 inches to about 4 inches.

A spine can comprise a material with a durometer from about 52 D to about 120 R, such as from about 52 D to about 85 D, such as from about 52 D to about 62 D.

In some cases, a spine may comprise a material with a durometer of about 55 D. A spine can comprise one or more polymers, such as a polymer selected from the group consisting of silicone; polyether block amide, polypropylene; nylon; polytetrafluoroethylene; polyethylene, ultra high molecular weight polyethylene; polycarbonates; polyolefins; polyurethanes; polyvinylchlorides; polyamides; polyimides; polyacrylates; polyphenolics; polystyrene; polycaprolactone; polylactic acid, polyglycolic acid; polyglycerol sebacate; hyaluric acid, silk fibroin collagen; elastin; poly(p-dioxanone), poly(3-hydroxybutyrate); poly (3-hydroxyvalerate); poly(valcrolactone); poly(tartronic acid); poly(beta-malonic acid); poly(propylene fumarates); a polyanhydride; a tyrosine-derived polycarbonate, a polyorthoester; a degradable polyurethane; a polyphosphazene; and any combination thereof. A spine can comprise the same material as fiber matrix, such as when both may comprise the same electrospun material.

A spine can comprise at least one thermoplastic co-polymer. A spine can comprise two or more materials, such as a first material and a second material harder than the first material. In some cases, a spine can comprise relatively equal amounts of a harder material and a softer material. The softer material can comprise polydimethylsiloxane and a polyether-based polyurethane and the harder material can comprise aromatic methylene diphenyl isocyanate. A spine can comprise one or more drugs or other agents, such as one or more agents constructed and arranged to be released over time.

In some cases, a spine may comprise a metal material, such as a metal selected from the group consisting of: nickel titanium alloy; titanium alloy; titanium; stainless steel; tantalum; magnesium; cobalt-chromium alloy; gold; platinum; and combinations thereof. In some cases, a spine may comprise a reinforced resin, such as a resin reinforced with carbon fiber and/or Kevlar. In some cases, at least a portion of a spine may be biodegradable, such as when a spine may comprise a biodegradable material such as a biodegradable metal or biodegradable polymer. In some cases, fiber matrix can comprise a biodegradable material and/or a non-biodegradable material. In some cases, a spine may not comprise a biodegradable material. In some cases, fiber matrix can comprise a biodegradable material and/or a non-biodegradable material.

A spine can be configured to biodegrade over time such as to provide a temporary kink resistance or other function to device. In some cases, a spine can temporarily provide kink resistance to graft device for a period of less than about twenty-four hours. In some cases, a spine can provide kink resistance to graft device for a period of less than about one month. In some cases, a spine can provide kink resistance to graft device for a period of less than about six months.

A spine can comprise a polymer constructed and arranged to change one or more properties upon exposure to an external stimuli. The polymer can comprise a polymer selected from the group consisting of: N-isopropylacrylamide (NIPAAm); a polaxamer (Pluronics), and any combination thereof. The external stimuli can comprise a stimuli selected from the group consisting of: temperature; pH; light; magnetic field; electric field; exposure to a solvent; and any combination thereof. The changed property can comprise a property selected from the group consisting of: hydrophobicity; a material property; an adhesive property; size; geometry; and combinations thereof. For instance, spine can exhibit an increase of hydrophobicity when exposed to a stimuli such as an electromagnetic field, such as an electromagnetic field that may be provided during an electrospinning process as described herein.

A spine can comprise one or more coatings. A coating can cover all or a portion of one or more filaments. A spine can comprise an inner surface and an outer surface, and coating can be positioned on inner surface, on outer surface, and/or on another surface of spine A coating can comprise an adhesive element or otherwise exhibit adhesive properties, such as a coating comprising a material selected from the group consisting of: fibrin gel; starch-based compound; mussel adhesive protein; and any combination thereof. A coating can be constructed and arranged to provide a function selected from the group consisting of: anti-thrombogenecity; anti-proliferation; anti-calcification; vasorelaxation; and any combination thereof. A coating can comprise a dehydrated gelatin, such as a dehydrated gelatin coating configured to hydrate to cause adherence of spine to conduit. A coating can comprise a hydrophilic and/or a hydrophobic coating. A coating can comprise a radiopaque coating, in some cases, a spine may comprise at least a portion that may be radiopaque, such as when spine may comprise a radiopaque material such as barium sulfate.

A spine can be constructed and arranged to be cut to length during the manufacturing process, such as at a time after application of at least a portion of fiber matrix. A spine can be cut with one or more tools, such as trimming tool.

Spine 510 can comprise at least three projections 511, such as at least six projections 511. In some cases, spine 510 may include at least two projections 511 for every about 15 mm of length of spine 510, such as at least about two projections 511 for every about 7.5 mm of length of spine 510, or at least about two projections for every about 2 mm of length of spine 510. In some cases, spine 510 may comprise about two projections 511 for each about 6.5 mm of length of spine 510. In some cases, a series of projections 511 may be positioned about 0.125 inches from each other.

Spine 510 can comprise one or more continuous filaments 516, such as three or less continuous filaments, two or less continuous filaments, or a single continuous filament. In some cases, spine 510 may comprise a continuous filament 516 of at least about 15 inches long (i.e. the curvilinear length), or at least about 30 inches long, such as when spine 510 comprises a length of about 3.5 inches. In some cases, filament 516 may comprise a length (e.g. a continuous curvilinear length or a sum of segments with a cumulative curvilinear length) of about 65 inches (e.g. to produce an about 4.0 mm diameter spine 510), or a length of about 75 inches (e.g. to produce an about 4.7 mm diameter spine 510), or a length of about 85 inches (e.g. to produce an about 5.5 mm diameter spine 510). Filament 516 can comprise a relatively continuous cross section, such as an extruded or molded filament with a relatively continuous cross section. Spine 510 can comprise a filament 516 including at least a portion with a cross sectional geometry selected from the group consisting of: elliptical; circular; oval; square; rectangular; trapezoidal; parallelogram-shaped; rhomboid-shaped; T-shaped; star-shaped; spiral-shaped; (e.g. a filament comprising a rolled sheet), and any combination thereof or other geometries. Filament 516 can comprise a cross section with a major axis from about 0.2 mm to about 1.5 mm in length, such as a circle or oval with a major axis less than or equal to about 1.5 mm, less than or equal to about 0.8 mm, or less than or equal to about 0.6 mm, or from about 0.4 mm to about 0.5 mm. Filament 516 can comprise a cross section with a major axis greater than or equal to about 0.1 mm, such as a major axis greater than or equal to about 0.3 mm. In some cases, the major axis and/or cross sectional area of filament 516 may be proportionally based to the diameter of spine 510 (e.g. a larger spine 510 diameter may correlate to a larger filament 516 diameter, such as when a range of different diameter spine 510's may be provided in a kit).

Filament 516 can be a single core, monofilament structure. In some cases, filament 516 can comprise multiple filaments, such as a braided multiple filament structure. In some cases, filament 516 can comprise an injection molded component or a thermoset plastic component, such as when spine 510 comprises multiple projections 511 that may be produced at the same time as the creation of one or more filaments 516 (e.g. when filament 516 may be created in a three-dimensional biased shape).

Filament 516 can comprise a 3D printed component, an extruded component, a molded component, and/or an electrospun component, such as a component produced by the same device used to produce covering 110 (e.g. MDD 300), such as when spine 510 and covering 110 may comprise the same or similar materials.

Spine 510 can comprise a material with a durometer from about 40 D to about 120R, such as from about 50 D to about 85 D, such as from about 52 D to about 62 D in some cases, spine 510 may comprise a material with a durometer of about 55). Spine 510 can comprise one or more polymers, such as a polymer selected from the group consisting of: silicone; polyether block amide; polypropylene; nylon; polytetrafluoroethylene; polyethylene; ultra-high molecular weight polyethylene; polycarbonates; polyolefins; polyurethanes; polyvinylchlorides; polyamides; polyimides; polyacrylates; polyphenolics; polystyrene; polycaprolactone; polylactic acid, polyglycolic acid; polyglycerol sebacate; hyaluronic acid; silk fibroin collagen; elastin; poly(p-dioxanone); poly(3-hydroxybutyrate); poly(3-hydroxyvalerate); poly(valecrolactone); poly(tartronic acid); poly(beta-malonic acid), poly(propylene fumarates), a polyanhydride; a tyrosine-derived polycarbonate, a polyorthoester; a degradable polyurethane; a polyphosphazene; and any combination thereof or other materials.

Spine 510 can comprise the same or substantially similar material(s) as covering 110. Spine 510 can comprise at least one thermoplastic co-polymer. Spine 510 can comprise two or more materials, such as a first material and a second material harder than the first material. In some cases, spine 510 may comprise relatively equal amounts of a harder material and a softer material. The softer material can comprise polydimethylsiloxane and a polyether-based polyurethane, and the harder material can comprise aromatic methylene diphenyl isocyanate. Spine 510 can comprise one or more drugs or other agents, such as one or more agents constructed and arranged to be released over time.

In some cases, spine 510 may comprise a metal material, such as a metal selected from the group consisting of: a nickel titanium alloy; a titanium alloy; titanium; stainless steel; tantalum; magnesium; cobalt-chromium alloy; gold; platinum; and any combination thereof or other materials. In some cases, spine 510 may comprise a reinforced resin, such as a resin reinforced with carbon fiber and/or Kevlar. In some cases, at least a portion of spine 510 may be biodegradable, such as when spine 510 may comprise a biodegradable material such as a biodegradable metal or biodegradable polymer. In some cases, covering 110 can comprise a non-biodegradable material. In some cases, spine 510 may not comprise a biodegradable material.

Spine 510 can be configured to biodegrade over time such as to provide a temporary kink resistance or other function to graft device 100. In one embodiment, spine 510 can temporarily provide kink resistance to graft device 100 for a period of less than about twenty-four hours. In an alternative embodiment, spine 510 can provide kink resistance to graft device 100 for a period of less than about one month. In yet another embodiment, spine 510 can provide kink resistance to graft device 100 for a period of less than about six months. Numerous forms of biodegradable materials can be employed. Bolz et al. (U.S. Pat. No. 6,287,332) discloses a biodegradable implant which may include a combination of metal materials that can be an alloy or a local galvanic element. Metal alloys can consist of at least a first component which forms a protecting passivation coat and a second component configured to ensure sufficient corrosion of the alloy. The first component may be at least one component selected from the group consisting of: magnesium, titanium, zirconium, niobium, tantalum, zinc and silicon, and the second component is at least one metal selected from the group consisting of: lithium, sodium, potassium, manganese, calcium and iron. Furst et al. (U.S. patent application Ser. No. 11/368,298) discloses an implantable device at least partially formed of a bioabsorbable metal alloy that includes a majority weight percent of magnesium and at least one metal selected from calcium, a rare earth metal, yttrium, zinc and/or zirconium. Doty et al. (U.S. patent application Ser. No. 11/744,977) discloses a bioabsorbable magnesium reinforced polymer stent that includes magnesium or magnesium alloys Numerous biodegradable polymers can be used such as are described herein.

System 10 can include drying assembly 650, which can be constructed and arranged to remove moisture or other fluids from conduit 120 and/or covering 110, such as to remove solvent from locations surrounding conduit 120 and/or covering 110. Drying assembly 650 can comprise a heat generator, dehydrator, desiccant or other fluid absorbing material, and/or other mechanism may be configured to remove solvent from locations on, within, and/or proximate conduit 120 and/or covering 110. Drying assembly 650 can comprise a handheld device. In some cases, conduit 120 may comprise harvested tissue (e.g. a harvested saphenous vein segment) and drying assembly 650 may comprise gauze or other material used to manually remove fluids from conduit 120, such as to remove solvents and/or improve adherence between covering 110 and conduit 120.

MDD 300 can include one or more modification assemblies constructed and arranged to modify one or more components and/or one or more portions of graft device 100 in the illustrated embodiment, MDD 300 may include modification assembly 605. Modification assembly 605 may comprise a nozzle assembly or other modifying element, modifying element 627. Modification assembly 605 may comprise linear drive assembly 645. Assembly 605 may be operably attached to linear drive assembly 645, which may be configured to translate assembly 605 in at least one direction, such as a reciprocating motion in back and forth directions spanning a distance similar to $D_{SWEEP}$ of linear drive assembly 345. Assembly 605 can be operably attached to supply 620 via delivery tube 625.

Modification assembly 605 can be configured to remove vapor from about conduit 120 and/or covering 110, such as to reduce the amount of solvent in conduit 120 and/or covering 110. In some cases, supply 620 can comprise a vacuum that enables modifying element 627 (e.g. a nozzle) to extract gas and/or vapor via delivery tube 625.

System 10 can include one or more graft device 100 modifying agents, such as agent 602 shown. Agent 602 can comprise a solvent configured to perform a surface modification, such as a solvent selected from the group consisting of dimethylformamide; hexafluoroisopropanol; tetrahydrofuran; dimethyl sulfoxide; isopropyl alcohol; ethanol; and any combination thereof or other solvents. In some cases, system 10 may be constructed and arranged to perform a surface modification configured to enhance the adhesion of two or more of: conduit 120, spine 510 and covering 110. In some cases, system 10 may be constructed and arranged to perform a surface modification to covering 110 and/or spine 510 to cause a modification of the surface energy of covering 110 and/or spine 510, respectively. In some cases, the surface of spine 510 may be modified with a heated die comprising a textured or otherwise non-uniform surface. In some cases, MDD 300 and/or another component of system 10 may comprise a radiofrequency plasma glow discharge assembly constructed and arranged to perform a surface modification of spine 510, such as a process performed in the presence of a material selected from the group consisting of: hydrogen; nitrogen; ammonia, oxygen, carbon dioxide, C2F6; C2F4, C3F6; C2H4, CH4; and any combination thereof or other materials.

Supply 620 can comprise one or more of: a reservoir of one or more agents, such as agent 602; a power supply such as a laser power supply; and/or a reservoir of compressed fluid. In some cases, modifying element 627 may comprise a nozzle, such as a nozzle configured to deliver a covering 110 modifying agent, a conduit 120 modifying agent, a spine 510 modifying agent, and/or a graft device 100 modifying agent.

For clarification, any reference to a "nozzle" or "assembly", in singular or plural form, can include one or more nozzles, such as one or more nozzles 310 or one or more modifying elements 627 configured as a nozzle, or one or more assemblies, such as one or more material delivery assemblies 305 or one or more modification assemblies 605.

In some cases, modifying element 627 may be configured to deliver agent 602. For example, agent 602 can comprise a wax, gel (e.g. a pluronic gel or other poloxamer gel) or other protective material delivered to conduit 120 prior to the application of covering 110 to conduit 120, the delivered agent 602 may be configured to protect conduit 120 from adverse effects of covering 110 (e.g. protection from one or more solvents or other potentially harmful materials of covering 110) In some cases, agent 602 can comprise a neutralizing material (e.g. a material configured to neutralize adverse effects of potentially harmful materials), the agent 602 may be delivered to conduit 120 prior to and/or during the application of covering 110 to conduit 120. This delivery of agent 602 can be performed to prevent or otherwise minimize exposure of conduit 120 to one or more solvents (e.g. hexafluoro-2-propanol (HFIP)) may be included in material 350, and/or to reduce injury to conduit 120 by any solvent.

An agent 602 comprising a solvent-reducing material and/or a solvent neutralizing material can be delivered via mandrel 320 (e.g. when mandrel 320 comprises a porous mandrel), via modifying element 627, and/or via a separate device. Agent 602 can be applied to one or more surfaces of conduit 120 via a method selected from the group consisting of: spraying; dipping; dripping; brushing, and any combination thereof. Agent 602 can be applied to conduit 120 prior to and/or after placing conduit 120 around mandrel 320. In some cases, agent 602 may comprise a solvent-reducing material comprising a thermogelling fluid, such as pluronic 407 poloxamer gel, or an equivalent, configured as a barrier. An agent 602 comprising a thermogel can be applied at a temperature below the solution gelation temperature such that the solution is a liquid during application and gels on a surface of conduit 120. In some cases, the thermogel can be gelled prior to application onto conduit 120. In some cases, an agent 602 comprising a gel or other material may be applied at a thickness from about 0.1 mm to about 2 mm to one or more surfaces (e.g. the entire outer surface or a portion thereof such as a majority of the outer surface) of conduit 120.

Agent 602 can comprise a thermogel solution prepared using distilled or ionized water, or the thermogel can be prepared using a preservative solution (e.g. to increase the buffering capacity of the thermogel). Examples of applicable preservative solutions may include but are not limited to: phosphate buffered saline (PBS), cell culture media (e.g. Dulbecco's Modified Eagle Media or Gibco RPMI 1640); balanced salt solution (e.g. lactated ringer's solution or Hank's Balanced Salt solution); and/or a cardioplegia solution. Agent 602 can comprise one or more materials added to a thermogel solution, such as to perform a function selected from the group consisting of: increase buffering capacity of the solution; modify the pH of the solution; act as a solvent scavenger (e.g. an HFIP scavenger); and any combination thereof. For example, agent 602 can comprise: a salt (e.g. a sodium or potassium salt), sodium bicarbonate; powdered cell culture media; uridine diphosphate glucuronic acid; and any combination thereof. Following application of covering 110 onto conduit 120, agent 602 can be left in place during implantation of graft device 100. In some cases, graft device 100 can be placed in a solution (e.g a cooled vein preservation solution), to re-liquefy agent 602 (e.g. re-liquefy a thermogel material component of agent 602) such that it can be removed from graft device 100.

Application of agent 602 (e.g. a poloxamer gel) onto a surface (e.g. the outer surface) of conduit 120 as a temporary layer between covering 110 and conduit 120 may provide numerous advantages. In some cases, agent 602 comprising a gel or other material can provide an adhesive connection between conduit 120 and covering 110, such as to improve post-application handling of conduit 120. In some cases, agent 602 may be applied as a temporary layer on the inner surface of conduit 120, with sufficient thickness to allow a smaller diameter mandrel 320 to be used. In some cases, trauma to conduit 120 (e.g a vein) can be reduced.

In some cases, modifying element 627 may be configured to deliver a kink resisting element, for example spine 510, such as a robotic assembly constructed and arranged to laterally deliver spine 510 about at least conduit 120 (e.g. about conduit 120 and an inner layer of covering 110) In some cases, modifying element 627 can be configured to modify conduit 120, spine 510 and/or covering 110, such as to cause graft device 100 to be kink resistant or otherwise enhance the performance of the graft device 100 produced by system 10. In these graft device 100 modifying cases, modifying element 627 can comprise a component selected from the group consisting of: a robotic device such as a robotic device configured to apply spine 510 to conduit 120; a nozzle, such as a nozzle configured to deliver agent 602; an energy delivery element, such as a laser delivery element such as a laser excimer diode or CO2 laser, or another element configured to trim one or more components of graft device 100; a fluid jet, such as a water jet or air jet configured to deliver fluid during the application of covering 110 to conduit 120; a cutting element, such as a cutting element configured to trim spine 510 and/or covering 110; a mechanical abrader; and any combination thereof or other components. Modification of covering 110 or other graft device 100 component by modifying element 627 can occur during the production of covering 110 and/or after covering 110 has been applied to conduit 120. Modification of one or more spines 510 can be performed prior to and/or after spine 510 has been applied to surround conduit 120. In some cases, modifying element 627 can be used to cut or otherwise trim covering 110 and/or a spine 510.

In an alternative embodiment, modification assembly 605 of system 10 can be an additional component or assembly, separate from MDD 300, such as a handheld device configured to remove solvent and/or deliver spine 510. In some cases, modification assembly 605 may comprise a handheld laser, such as a laser device which can be hand operated by an operator. In some cases, modification assembly 605 may comprise a fan, vacuum or other gas propelling device configured to remove solvent or other undesired material from areas surrounding conduit 120 and/or covering 110. Modification assembly 605 can be used to modify graft device 100 after its removal from MDD 300, such as prior to and/or during a graft device 100 implantation procedure.

Laser or other modifications to covering 110 can cause portions of covering 110 to undergo physical changes, such as hardening, softening, melting, stiffening, creating a resilient bias, expanding, and/or contracting, and/or can also cause covering 110 to undergo chemical changes, such as forming chemical bonds with an adhesive layer between the outer surface of conduit 120 and covering 110 and/or a chemical change that reduces the amount of solvent in covering 110. In some cases, modifying element 627 may be configured to modify conduit 120, such that conduit 120 may comprise a kink resisting or other performance enhancing element. Modifications to conduit 120 can include but are not limited to a physical change to one or more portions of conduit 120 selected from the group consisting of drying; hardening; softening, melting; stiffening; creating a resilient bias; expanding; contracting; and any combination thereof or other changes. Modifications of conduit 120 can cause conduit 120 to undergo chemical changes, such as a chemical change that results in a reduction in solvent in covering 110 and/or a chemical change that forms chemical bonds with an adhesive layer between an outer surface of conduit 120 and spine 510 and/or covering 110.

Covering 110 can include an inner layer and an outer layer. The inner layer can include an adhesive component and/or exhibit adhesive properties. The inner layer can be delivered separate from the outer layer, for example, delivered from a separate nozzle or at a separate time during the process of creating covering 110. Selective adhesion between the inner and outer layers can be configured to provide kink resistance. Spine 510 can be placed between the inner and outer layers of covering 110, such as is described herein.

In some cases, MDD 300 can be configured to deliver covering 110 and/or an adhesive layer according to set parameters configured to produce a kink resistant element in and/or provide kink resisting properties to graft device 100. For example, an adhesive layer can be delivered to conduit 120 for a particular length of time, followed by delivery of material 350 for another particular length of time. An application parameters may include but may not be limited to: amount of adhesive layer and/or material 350 delivered; rate of adhesive layer and/or material 350 delivered; nozzle 310 distance to mandrel 320 and/or conduit 120; linear travel distance of nozzle 310 or a fiber modifying element 627 along its respective drive assembly (for example, linear drive assembly 345 or 645); linear travel speed of nozzle 310 or a fiber modifying element 627 along its respective drive assembly; compositions of material 350 and/or adhesive layer; concentrations of material 350 and/or adhesive layer; solvent compositions and/or concentrations; covering 110 inner and outer layer compositions and/or concentrations; spontaneous or sequential delivery of material 350 and the adhesive layer; flow rate of material 350 delivered to nozzle 310; pressure of material delivered to nozzle 310; temperature of nozzle 310; voltage applied to nozzle 310; voltage applied to mandrel 320; temperature of mandrel 320; viscosity of material 350; temperature within chamber 20; relative humidity within chamber 20; airflow within chamber 20; and any combination thereof or other parameters.

Nozzle 310 can be constructed of stainless steel, such as passivated 304 stainless steel. A volume of space surrounding nozzle 310 can be maintained free of objects or substances which can interfere with the material 350 delivery process. Nozzle 310 geometry and orientation, as well as the temperature, pressure and/or electrical potential voltages (e.g. as applied between nozzle 310 and mandrel 320) can be chosen to control production of covering 110.

Mandrel 320 can be positioned in a particular spaced relationship from assembly 305 and/or assembly 605, and nozzle 310 and/or modifying element 627, respectively. In the illustrated embodiment, mandrel 320 may be positioned above and below assemblies 605 and 305, respectively. In some cases, mandrel 320 can be positioned above, below, to the right and/or to the left of, assembly 305 and/or assembly 605. The distance between mandrel 320 and the tip of nozzle 310 and/or modifying element 627 can be less than about 20 centimeter (cm), or less than about 15 cm, such as a distance of from about 12.2 cm to about 12.8 cm or about 12.5 cm. In some cases, multiple nozzles 310 and/or multiple modifying elements 627, for example components of similar or dissimilar configurations, can be positioned in various orientations relative to mandrel 320. In some cases, the distance between nozzles 310 and/or modifying elements 627 and mandrel 320 may vary along the length of their respective travel along mandrel 320, such as to create a varying pattern of covering 110 along conduit 120. In some cases, nozzle 310 and/or modifying element 627 distances from mandrel 320 can vary continuously during the application of material 350 and/or the distance can vary for one or more set periods of time during the process.

In some cases, an electrical potential may be applied between nozzle 310 and one or both of conduit 120 and mandrel 320 (e.g. when MDD 300 may comprise at least an electrospinning device, such as to create at least a portion of covering 110 and/or a spine 510). The electrical potential can draw at least one fiber from material delivery assembly 305 to conduit 120. Conduit 120 can act as the substrate for an electrospinning process, collecting the fibers that may be drawn from material delivery assembly 305 by the electrical potential. In some cases, mandrel 320 and/or conduit 120 may have a lower voltage than nozzle 310 to create the desired electrical potential. For example, the voltage of mandrel 320 and/or conduit 120 can be a negative or zero voltage while the voltage of nozzle 310 can be a positive voltage. Mandrel 320 and/or conduit 120 can have a voltage of about −5 kiloVolts (kV) (e.g, about −10 kV, −9 kV, −8 kV, −7 kV, −6 kV, −5 kV, −4.5 kV, −4 kV, −3.5 kV, −3.0 kV, −2.5 kV, −2 kV, −1.5 kV, or −1 kV) and the nozzle 310 can have a voltage of about +15 kV (e.g, about 2.5 kV, 5 kV, 7.5 kV, 12 kV, 13.5 kV, 15 kV, 17 kV, or 20 kV). In some cases, the potential difference between nozzle 310 and mandrel 320 and/or conduit 120 can be from about 5 kV to about 30 kV. This potential difference may draw fibers from nozzle 310 to conduit 120. In some cases, nozzle 310 may be electrically charged with a potential of between +15 kV and +17 kV while mandrel 320 may be at a potential of about −2 kV. In some cases, mandrel 320 may be a fluid mandrel, such as the fluid mandrel described in applicant's U.S. Pat. No. 9,656, 417, issued May 23, 2017, the content of which is incorporated herein by reference in its entirety for all purposes.

Mandrel 320 can be configured to rotate about an axis, such as central axis 335 of mandrel 320, with axis 328 of nozzle 310 may be oriented orthogonal to axis 335. In some cases, axis 328 of nozzle 310 may be horizontally offset from axis 335. The rotation around axis 335 may allow covering 110 to be applied along all sides, or around a portion of an entire circumference of conduit 120 in some cases, two motors 341 a and 341 b may be used to rotate mandrel 320. In some cases, MDD 300 can include a single motor configured to rotate mandrel 320. In some cases, mandrel 320 may not be rotated (e.g. when mandrel 320 may be a flat plate). The rate of rotation of mandrel 320 can determine how fibers may be applied to one or more segments of conduit 120. For example, for a thicker portion of covering 110, the rotation rate can be slower than when a thinner portion of covering 110 is desired. In some cases, mandrel 320 may be rotated at a rate (e.g. a minimum, maximum or average rate) of from about 100 rotations per minute (rpm) to about 500 rpm, such as a rate of from about 200 rpm to about 300 rpm, from about 240 rpm to about 260 rpm, or about 250 rpm.

In addition to mandrel 320 rotating around axis 335, the material delivery assembly 305 can move, such as when driven by linear drive assembly 345 in a reciprocating or oscillating horizontal motion (to the left and right of the page). Drive assembly 345, as well as linear drive assembly 645 which operably attaches to assembly 605, can individually or collectively comprise a linear drive assembly, such as a belt-driven and/or gear-driven drive assembly comprising two or more pulleys driven by one or more stepper motors. In some cases, assemblies 305 and/or 605 can be constructed and arranged to rotate around axis 335, rotating element not shown. The length of linear drive assemblies 345 and/or 645 and the linear motion applied to assemblies 305 and 605, respectively, can vary based on the length of conduit 120 to which a covering 110 is produced and/or a covering 110 modification is applied. For example, the supported linear motion of linear drive assemblies 345 and/or 645 can comprise a translation distance of from about 10 centimeter (cm) to about 50 cm, such as to cause a translation of assembly 305 and/or 605 from about 27 cm to about 31 cm, or about 29 cm. Rotational speeds of mandrel 320 and translational speeds of assemblies 305 and/or 605 can be relatively constant, or can be varied during the material 350 delivery process of assembly 305 and/or modification procedure of assembly 605. In some cases, assemblies 305 and/or 605 may be translated (e.g. back and forth) at a relatively constant translation rate from about 40 millimeters per second (mm/sec) to about 150 mm/sec, such as to cause nozzle 310 and/or modifying element 627 to translate at a rate of from about 50 millimeter per second (mm/sec) to about 80 mm/sec, from about 55 mm/sec to about 65 mm/sec, or about 60 mm/sec, during the majority of its travel. In some cases, system 10 may be constructed and arranged to rapidly change directions of translation (e.g. by maximizing deceleration before a direction change and/or maximizing acceleration after a direction change).

Assemblies 305 and/or 605 can move along the entire length and/or along specific portions of the length of conduit 120. In some cases, delivery of material 350 and/or a modification may be applied to a length coordinating to a portion or the entire length of conduit 120 plus an additional about 5 cm (e.g. applied to mandrel 320). In another embodiment, material 350 and/or a modification may be applied to a length coordinating to a portion or the entire length of conduit 120 plus at least about 1 cm. Assemblies 305 and/or 605 can be controlled such that specific portions along the length of conduit 120 may be reinforced with a greater amount (e.g. thicker segment) of covering 110 as compared to other or remaining portions. In some cases, assemblies 305 and/or 605 can be controlled such that specific portions of the length of conduit 120 may include one or more kink resistant elements (e.g. one or more spines 510) positioned at those one or more specific conduit 120 portions. In addition, conduit 120 can be rotating around axis 335 while assemblies 305 and/or 605 move, via linear drive assemblies 345 and/or 645, respectively, to position assemblies 305 and/or 605 at the particular portion of conduit 120 and/or mandrel 320 to which material 350 may be delivered and/or covering 110 may be modified.

System 10 can also include a power supply, power supply 302 configured to provide power to material delivery assembly 305 (e.g. to a pump or other fluid propulsion mechanism of material delivery assembly 305). Power supply 302 can be configured to provide electric potentials to nozzle 310 and mandrel 320, and/or to supply power to other components of system 10 such as linear drive assemblies 345 and 645 and assembly 605. Power supply 302 can be connected, either directly or indirectly, to at least one of mandrel 320 or conduit 120. Power can be transferred from power supply 302 to one or more components (such as each component) by, for example, one or more wires.

System 10 can include an environmental control assembly including environmental chamber, chamber 20, that may surround MDD 300 (e.g at least during the creation of covering 110) System 10 can be constructed and arranged to control the environmental conditions within chamber 20, such as to control one or more areas surrounding material delivery assembly 305 and/or mandrel 320 during the application of covering 110 to conduit 120. Chamber 20 can include inlet port assembly 21 and outlet port assembly 22. Inlet port assembly 21 and/or outlet port assembly 22 can include one or more components such as one or more components selected from the group consisting of: a fan; a source of a gas such as a dry compressed air source; a source of gas at a negative pressure; a vapor source such as a source including a buffered vapor, an alkaline vapor and/or an acidic vapor; a filter such as a high efficiency particulate air (HEPA) filter; a dehumidifier; a humidifier; a heater; a chiller; and electrostatic discharge reducing ion generator; and any combination thereof. Chamber 20 can include one or more environmental control components that can monitor and/or control temperature, humidity and/or pressure within chamber 20 (e.g. one or more environmental control components controlled by environmental controller 35). Chamber 20 can be constructed and arranged to provide relatively uniform ventilation about mandrel 320 (e.g. about conduit 120, covering 110 and/or spine 510) including an ultra-dry (e.g. ≤about 2 part per million (ppm) water or other liquid content) compressed gas (e.g. air) source may be configured to reduce humidity within chamber 20. Inlet port assembly 21 and outlet port assembly 22 can be oriented to purge air from the top of chamber 20 to the bottom of chamber 20 (e.g. to remove vapors of one or more solvents such as hexafluoro-2-propanol (HFIP), which can tend to settle at the bottom of chamber 20). Chamber 20 can be constructed and arranged to replace the internal volume of chamber 20 at least once every about 3 minutes, or once every about 1 minute, or once every about 30 seconds outlet port assembly 22 can include one or more filters 24 (e.g. replaceable cartridge filters) which may be suitable for retaining solvent or other potentially harmful components of material 350

(e.g. by filtering vapor including solvent) or to retain other undesired materials evacuated from chamber 20. In some cases, inlet port assembly 21 can include one or more filters 23 which are similarly suitable for retaining solvent or other undesired materials delivered into chamber 20. Chamber 20 can be constructed and arranged to maintain a flow rate through chamber 20 of at least about 30 liters per minute (L/min), such as at least about 45 L/min or at least about 60 L/min, such as during an initial purge procedure. Subsequent to an initial purge procedure, a flow rate of at least about 5 L/min, at least about 10 L/min, at least about 20 L/min or at least about 30 L/min can be maintained, such as to maintain a constant humidity level (e.g. a relative humidity from about 20% to about 24%) Chamber 20 can be constructed and arranged to control temperature, such as to control temperature within chamber 20 to a temperature from about 15° C. to about 25° C., such as from about 16° C. to about 20° C. with a relative humidity from about 20% to about 24%. In some cases, one or more objects or surfaces within chamber 20 may be constructed of an electrically insulating material and/or may not include sharp edges or exposed electrical components. In some cases, one or more metal objects may be positioned within chamber 20 and may be electrically grounded and/or maintained at a particular desired voltage level (e.g. a voltage level different than the voltage level of nozzle 310 and/or different than the voltage level of mandrel 320).

In some cases, system 10 may be configured to produce a first graft device, graft device 100' based on one or more component or process parameters. In some cases, graft device 100' may comprise conduit 120' and a covering 110' applied by MDD 300 (e.g. a 3D printer or other layered deposition device). Covering 110' can be produced by material delivery assembly 305 supplied with material 350, such as at a flow rate of about 15 milliliter per hour (ml/hr) Cumulative application time of covering 110' can comprise an approximate time period of from about 11 minutes and 40 seconds to about 17 minutes and 30 seconds. The cumulative application time of covering 110' can comprise a time period of from about 11 minutes and 40 seconds when conduit 120' may comprise an outer diameter of from about 3.4 millimeter (mm) to about 4.2 mm, a time period of about 14 minutes and 0 seconds when conduit 120' may comprise an outer diameter from about 4.2 mm to about 5.1 mm, and/or a time period of about 17 minutes and 30 seconds when conduit 120' may comprise an outer diameter from about 5.1 mm to about 6.0 mm.

Covering 110' can comprise an average fiber size of about 7.8 micrometer (μm), such as a population of fiber diameters with an average fiber size of about 7.8 μm with a standard deviation of about 0.45 μm. Covering 110' can comprise an average porosity of about 50.4%, such as a range of porosities with an average of about 50.4% and a standard deviation of about 1.1%. Covering 110' can comprise a strength property selected from the group consisting of: stress measured at about 5% strain comprising a level from about 0.4 megapascal (MPa) to about 1.1 MPa; ultimate stress at a level of from about 4.5 MPa to about 7.0 MPa; ultimate strain at a level of from about 200% to about 400%; and any combination thereof. Covering 110' can comprise a compliance from about $0.2 \times 10^{-4}$/mmHg to about $3.0 \times 10^{-4}$/mmHg when measured in arterial pressure ranges covering 110' can comprise an elastic modulus from about 10 MPa to about 15 MPa Covering 110' can be constructed and arranged with a targeted suture retention strength, such as an approximate suture retention strength of from about 2.0 Newton (N) to about 4.0 N with 6-0 Prolene® suture (or equivalent) and/or from about 1.5 N to about 3.0 N with 7-0 Prolene® suture (or equivalent) In some cases, graft device 100' may include a spine 510', such as a spine 510' placed between inner and outer layers of covering 110' (e.g. placed after one-third of the total thickness of covering 110' may be applied about conduit 120' or otherwise produced).

In some cases, system 10 may be configured to produce a second graft device, graft device 100" based on one or more component or process parameters. In some cases, graft device 100" may comprise conduit 120" and a covering 110" produced by MDD 300. Covering 110" can be applied via material delivery assembly 305 supplied with material 350 at a flow rate of about 20 milliliter per hour (ml/hr). Cumulative application time of covering 110" can comprise an approximate time period of from about 9 minutes and 30 seconds to about 13 minutes and 40 seconds. The cumulative application time of covering 110" can comprise a time period of about 9 minutes and 30 seconds when conduit 120" may comprise an outer diameter from about 3.4 millimeters (mm) to about 4.2 mm; a time period of about 11 minutes and 30 seconds when conduit 120" may comprise an outer diameter from about 4.2 mm to about 5.1 mm, and/or a time period of about 13 minutes and 40 seconds when conduit 120" may comprise an outer diameter from about 5.2 mm to about 6.0 mm.

Covering 110" can comprise an average fiber size of about 8.6 micrometer (μm), such as a population of fiber diameters with an average fiber size of about 8.6 μm with a standard deviation of about 0.45 μm. Covering 110" can comprise an average porosity of about 46.9%, such as a range of porosities with an average of about 46.9% and a standard deviation of about 0.9%. Covering 110" can comprise a strength property selected from the group consisting of: stress at about 5% strain comprising a level from about 0.6 MPa to about 1.3 MPa; ultimate stress at a level of from about 5.0 MPa to about 7.5 MPa; ultimate strain at a level of from about 200% to about 400%; and any combination thereof. Covering 110" can comprise a compliance from about $0.2 \times 10^{-4}$/mmHg to about $3.0 \times 10^{-4}$ mmHg when measured in arterial pressure ranges covering 110" can comprise an elastic modulus from about 12 MPa to about 18 MPa. Covering 110" can be constructed and arranged with a targeted suture retention strength, such as an approximate suture retention strength of from about 2.3 Newton (N) to about 4.3 N with 6-0 Prolene® suture and/or from about 2.0 N to about 3.5 N with 7-0 Prolene® suture. In some cases, graft device 100" may include a spine 510", such as a spine 510" placed between inner and outer layers of covering 110" (e.g. placed after one-third of the total thickness of covering 110" may be applied about conduit 120" or otherwise produced).

Coverings 110' and 110" can comprise one or more similar features and/or one or more dissimilar features. Covering 110" of graft device 100" can comprise more bonds between fibers than covering 110' of graft device 100'. The increased number of bonds can result in a higher covering 110" density which can be configured to limit cellular infiltration into graft device 100" (e.g. to increase the graft durability in vivo). Covering 110" can comprise fibers that are flatter (i.e. more oval versus round) and/or denser than fibers of covering 110'. Covering 110" can have a greater resiliency than covering 110'.

System 10 can comprise one or more solvent-reducing materials, such as solvent-reducing material 640 shown positioned within supply 620 in some cases, modification assembly 605 may be configured to deliver solvent-reducing material 640 to conduit 120 and/or covering 110 (e.g. onto conduit 120 and/or covering 110). In some cases, solvent-reducing material 640 may comprise a material selected from the group consisting of a desiccant; a material configured to bond with solvent; a material configured to absorb solvent; a neutralizing agent configured to neutralize solvent (e.g. make less toxic or otherwise less harmful to the patient); and any combination thereof. In some cases, solvent-reducing material 640 may be delivered onto conduit 120 to create a barrier (e.g. a barrier layer) between conduit 120 and an applied layer of covering 110 comprising solvent. In some cases, solvent-reducing material 640 may comprise a material selected from the group consisting of desiccant; lipid, phospholipid; buffer; pH buffer; polyethylene; polytetrafluoroethylene (PTFE); fibrin; albumin; gelatin; oil; wax; polyethylene glycol (PEG); carbon particle; activated carbon particle; alkaline material; powder; carbon particles; polymer beads; polymer gel; wicking fibrous membrane; solvent capillary transport system; ionizing gas; plasma; and any combination thereof. In some cases, solvent-reducing material 640 may comprise a pH buffer and/or alkaline material configured to prevent undesired pH changes in conduit 120. In some cases, solvent-reducing material 640 may comprise an ionizing gas configured to absorb or otherwise neutralize solvent. For example, a "cloud" of ionizing gas may be positioned proximate the conduit 120 such that material delivered by material delivery assembly 305 pass through the ionizing gas and attenuate the negative effects of solvent.

In some cases, solvent-reducing material 640 may comprise a material positioned as a barrier between conduit 120 and covering 110. In some cases, solvent-reducing material 640 may comprise a removable or otherwise temporary barrier (e.g. a barrier removed prior to implantation of graft device 100 in the patient). In some cases, solvent-reducing material 640 may be applied to a surface of the conduit 120 and/or covering 110 (e.g. an inner layer of the covering 110). In some cases, solvent-reducing material 640 may be delivered to conduit 120 and/or covering 110 during application of material by material delivery assembly 305. In some cases, solvent-reducing material 640 may comprise a material configured to neutralize solvent, such as neutralizing agent 641 described herein.

System 10 can comprise one or more solvent neutralizing materials, such as solvent neutralizing material 641 shown positioned within supply 620. Solvent neutralizing material 641 can comprise a material configured to reduce injury to conduit 120 by solvent (e.g. when conduit 120 comprises a vein segment or other living tissue). In some cases, modification assembly 605 may be configured to deliver solvent neutralizing material 641 to conduit 120 and/or covering 110 (e.g. onto conduit 120 and/or covering 110), such as an application that may occur prior to the delivery of covering 110, during the delivery of covering 110 (e.g. delivered while material 350 may be delivered, or delivered to a partial layer of covering 110 when no material 350 may be applied) and/or after the delivery of covering 110. In some cases, solvent neutralizing material 641 may comprise a material selected from the group consisting of: a buffer; polyethylene; polytetrafluoroethylene (PTFE); fibrin; albumin; gelatin; polyethylene glycol (PEG); carbon particle; activated carbon particle; sulfate; phosphate; ADP; ATP converted from ADP, an acid reducing material; a lipid; a phospholipid; an acidophilic bacteria; an alkaliphilic bacteria; and any combination thereof. In some cases, solvent neutralizing material 641 may be positioned about at least a portion of conduit 120 and/or an inner layer of covering 110 to function as a barrier to prevent interaction between solvent and conduit 120. In some cases, the barrier can be configured to be removable (e.g. dissolvable or otherwise removable) prior to implantation of graft device 100 in the patient. In some cases, solvent neutralizing material 641 (and the resultant barrier) can comprise a material selected from the group consisting of lipid; phospholipid; buffer, pH buffer; polyethylene; PTFE; fibrin; albumin; gelatin; oil; wax; PEG; carbon particle; activated carbon particle; alkaline material; powder; carbon particles; polymer beads; polymer gel; and any combination thereof.

System 10 can comprise one or more solvent-reducing elements, such as solvent-reducing element 40 and/or solvent-reducing element 361 of FIG. 3. Solvent-reducing element 40, shown positioned in chamber 20, and solvent-reducing element 361, shown positioned in NIDD 300, can comprise one or more devices or components configured to extract solvent, such as to extract solvent from conduit 120 (e.g. from the wall of conduit 120), from covering 110 (e.g. from one or more layers of covering 110), and/or from locations surrounding these (e.g. one or more locations within chamber 20). Solvent-reducing element 40 and/or 361 can comprise a component selected from the group consisting of fan, nozzle; filter; electrostatic filter, osmotic membrane; fluid delivery element, fluid extraction element; vacuum applying element; agitating element; heating element; cooling element; sponge; diffusion enhancing element; desiccant; forced convection element; and any combination thereof. In some cases, solvent-reducing element 40 and/or 361 can comprise a solvent-reducing material (e.g. a material configured to reduce solvent or other undesired substance), such as a material selected from the group consisting of: a desiccant; a material configured to bond with solvent; a material configured to absorb solvent; a material configured to neutralize solvent (e.g make less toxic or otherwise less harmful to the patient); and any combination thereof.

In some cases, solvent-reducing element 40 and/or 361 may comprise a fluid extraction element configured to reduce solvent, such as a vacuum applying element. In some cases, nozzle 310 and/or modifying element 627 can comprise the solvent-reducing element configured to extract fluid and/or apply a vacuum. In some cases, solvent-reducing element 40 and/or 361 may comprise a temperature control element configured to reduce solvent, such as when environmental controller 35 may adjust or may otherwise control the temperature within chamber 20 to cause a reduction in solvent. In some cases, solvent-reducing element 40 and/or 361 may comprise a fluid delivery element configured to deliver a gas or other fluid proximate conduit 120 to remove solvent (e.g. when nozzle 310 and/or modifying element 627 comprise the solvent-reducing element delivering the fluid to enhance diffusion of solvent). In some cases, solvent-reducing element 40 and/or 361 comprise an agitating element, such as a fan or other agitating element proximate conduit 120 (e.g to create a stream of laminar or turbulent gas flow proximate conduit 120). In some cases, solvent-reducing element 40 and/or 361 may comprise a humidity control element configured to remove solvent. In some cases, solvent-reducing element 40 and/or 361 may comprise at least a replaceable portion (e.g. a disposable portion used on a single patient only). In some cases, solvent-reducing element 40 and/or 361 may comprise a translatable element, such as when nozzle 310 and/or modifying element 627 may comprise the solvent-reducing element and may be translated by linear drive assemblies 345 and/or 645, respectively. In some cases, solvent-reducing element 40 and/or 361 may comprise one or more elements configured to rotate and/or translate relative to conduit 120.

System 10 can comprise one or more sensors, such as one or more sensors configured to detect the presence or level of one or more solvents (e.g. sensors that produce a signal related to a solvent level). In some cases, chamber 20 may comprise sensor 26 comprising one or more sensors. In some cases, controller 30 may comprise sensor 36 comprising one or more sensors. In some cases, mandrel 320 may comprise sensor 329 comprising one or more sensors (e.g. a sensor configured to measure a parameter of conduit 120 such as a level of solvent). In some cases, material delivery assembly 305 may comprise sensor 309 comprising one or more sensors. In some cases, MDD 300 may comprise sensor 369 comprising one or more sensors. In some cases, modification assembly 605 may comprise sensor 606 comprising one or more sensors. Sensor 26, 36, 329, 309, 369 and/or 606 can individually or any combination thereof comprise one or more sensors configured to measure a parameter (e.g. configured to produce a signal related to the level of a solvent) and may produce a signal based on the measured parameter. In some cases, sensor 26, 36, 329, 309, 369 and/or 606 can be configured to measure the concentration or other amount of solvent present within conduit 120 (e.g. within a wall of conduit 120), covering 110 and/or a location within chamber 20. System 10 can be configured to adjust one or more system parameters based on the sensor signal produced by sensor 26, 36, 329, 309, 369 and/or 606. In some cases, system 10 can be configured to alert an operator that the level of solvent present in graft device 100 may be below a threshold (e.g. to indicate that graft device 100 may be ready for implantation based on a measured level of solvent detected).

In some cases, sensor 26, 36, 329, 309, 369 and/or 606 comprise one or more sensors selected from the group consisting of: optical sensor; temperature sensor; humidity sensor; pH sensor; ganged litmus paper instrument; strain gauge; accelerometer; load cell; electrochemical sensor; pressure sensor; chemical sensor; a color changing chemical sensor; a photoionization sensor; fluorine sensor; a temperature sensor configured to measure cooling of the conduit 120 (e.g to assess evacuation of solvent); one or more temperature sensors configured to measure the temperature difference between inlet port assembly 21 and outlet port assembly 22; a sensor configured to measure the weight of at least a portion of graft device 100; a sensor configured to measure the mass of at least a portion of graft device 100; a sensor configured to measure the acidity of at least a portion of graft device 100; a sensor configured to measure a parameter of the exhaust of chamber 20 (e.g. exhaust through outlet port assembly 22); and any combination thereof. System 10 can be configured to adjust one or more system parameters based on the one or more signals produced by one or more sensors 26, 36, 329, 309, 369 and/or 606. The one or more system parameters adjusted can comprise one or more parameters selected from the group consisting of temperature proximate the conduit 120; flow rate of fluid proximate the conduit 120; rotation rate of the conduit 120; translation rate of the conduit 120; rotation rate of material delivery assembly 305; translation rate of the material delivery assembly 305; a nozzle 310 to a mandrel 320 distance; and any combination thereof. The one or more system parameters can be adjusted prior to, during and/or ater delivery of covering 110 to conduit 120.

In some cases, sensor 26, 36, 329, 309, 369 and/or 606 may comprise one or more sensors configured to produce a signal representing a solvent parameter level (e.g. a solvent concentration or other quantitative assessment of the presence of solvent). System 10 can be configured to reduce solvent until the solvent parameter level reaches a threshold (e.g. falls below a maximum level). For example, system 10 can be configured to perform a function selected from the group consisting of: maintaining graft device 100 within chamber 20 (e.g. maintaining graft device 100 within chamber 20 in a sterile condition and/or under controlled environmental conditions); rotating the graft device 100 (e.g. rotating conduit 120 and at least a portion of covering 110); providing a flow of gas proximate the graft device 100; providing an elevated temperature proximate the graft device 100, providing a desiccant proximate the graft device 100; and any combination thereof.

In some cases, material delivery assembly 305 may be configured to deliver fibers with an aspect ratio above 1 and/or to deliver hollow fibers, such that solvent more rapidly evacuates the fiber. In some cases, material delivery assembly 305 may be configured to deliver fibers with an aspect ratio from about 1.01:1 to about 10:1.

In some cases, system 10 may comprise one or more functional elements, such as functional element 25 shown positioned on chamber 20. Functional element 25 can comprise an element configured to remove solvent and/or to reduce the effects of solvent on conduit 120 (e.g. a vein segment or other living tissue). In some cases, functional element 25 may comprise an element selected from the group consisting of fan; nozzle; filter; electrostatic filter; osmotic membrane; fluid delivery element; fluid extraction element; vacuum applying element; agitating element; heating element; cooling element; sponge; diffusion enhancing element; desiccant; forced convection element; and any combination thereof in some cases, functional element 25 may comprise one or more elements positioned in MDD 300 or another component of system 10.

In some cases, system 10 may be configured to reduce solvent by rotating the conduit 120. For example, system 10 can be configured to perform a rotation with or without the simultaneous delivery of fibers to conduit 120, such as by rotating at an increased rotational velocity during delivery of fibers, and/or a rotation that may occur while no fibers may be delivered by material delivery assembly 305 (e.g. a rotation after delivery of covering 110 may be complete). In some cases, system 10 may be configured to rotate conduit 120 and/or covering 110 at a minimum velocity (e.g. a constant or variable rate that may include a rate greater than about 250 rotations per minute (rpm)) for a minimum time period (e.g. longer than about 1 second), in order to sufficiently reduce the amount of solvent present in graft device 100. In some cases, system 10 may be configured to rotate covering 110 at a first rate while covering 110 may be being delivered by material delivery assembly 305, and to rotate covering 110 at a second rate (e.g. a higher rate) after the delivery of covering 110 may be completed.

While conduit 120 may be described in relation to a hollow, tubular structure, any geometry may be considered within the scope of the present disclosure, including both non-hollow and/or non-tubular structures. Similarly, while device 100 may be described in terms of a graft device or other device configured to fluidly connect two or more anatomical locations (e.g. two or more blood vessels), graft device 100 can comprise any type of implant for a patient. In some cases, graft device 100 may be configured as an implant used to replace, augment or otherwise treat cartilage, ligament, bone, a disc, soft tissue and/or other tissue of the patient.

The foregoing description and accompanying drawings set forth a number of examples of representative embodiments at the present time. Various modifications, additions and alternative designs may become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

What is claimed is:

1. A method for producing a graft device, comprising:
   (a) imaging an electrospun conduit;
   (b) producing image data of the imaged electrospun conduit;
   (c) generating a construction signal based on the produced image data; and
   (d) delivering a material to produce a covering about the electrospun conduit based on the generated construction signal, wherein the graft device comprises the covering positioned about the electrospun conduit, wherein at least one physical property of the covering is defined by thickness data of the electrospun conduit.

2. The method as set forth in claim 1, wherein the graft device comprises an implant selected from the group consisting of artery bypass graft, coronary artery bypass graft, dialysis graft, peripheral arterial bypass graft, great vessel replacement, great vessel bypass graft, esophageal graft, tracheal graft, bronchial graft, biliary duct graft, intestinal graft, organ transplant vascular connection graft, neuronal replacement implant, ligament graft, ligament replacement, tendon graft, tendon replacement, transplant organ coating, fallopian tube, urethra, ureter, cartilage, hip joint, shoulder joint, intervertebral disc, menisci, and any combination thereof.

3. The method as set forth in claim 1, wherein the material comprises one or more materials selected from the group consisting of: synthetic polymer, natural polymer, protein, metal, metal alloy, collagen, elastin, a glycosaminoglycan, a proteoglycan, an alginate, cellulose, gelatin, silk fibroin, fibrinogen, chitosan, an enzyme, fibronectin, glycerin, integrin, keratin, a vitamin, a carbohydrate, a monosaccharide, a disaccharide, a polysaccharide, a nucleoside, abductin, lignin, a glycolipid, a phospholipid, a sterol, shrilk, cobalt-chrome, nitinol, aluminum oxide, magnesium, iron, zinc, steel, titanium, vitalium, alacrite, platinum, gold, silver, copper, manganese, a polyester, a polyurethane, a polycarbonate, a polyether, a polysulfone, a polyamide, a polyetheramide, a polystyrene, a polybutadiene, a polyisoprene, a poly(methyl methacrylate), a polyanhydride, a polydimethylsiloxane, a polydioxanone, polyethylene, glycol, polyethylene terephthalate, a polyglycolide, a polyhydroxyalkanoate, polyimide, polytetrafluoroethylene, polyvinylidene fluoride, polyethylene, polypropylene, polyvinylfluoride, polyvinylchloride, polyacylonitrile, silicone, a ceramic, a bioceramic, a bioglass, a composite material, and any combination thereof.

* * * * *